(12) United States Patent
Serra et al.

(10) Patent No.: US 8,029,792 B2
(45) Date of Patent: Oct. 4, 2011

(54) TCR-INDEPENDENT ACTIVATION OF T CELLS

(75) Inventors: Alessandro Serra, Alghero (IT); Andreas Wack, Frankfurt am Main (DE)

(73) Assignee: Novartis Vaccines and Diagnostics SRL, Siena (IT)

( * ) Notice: Subject to any disclaimer, the term of this patent is extended or adjusted under 35 U.S.C. 154(b) by 354 days.

(21) Appl. No.: 11/919,955

(22) PCT Filed: May 8, 2006

(86) PCT No.: PCT/IB2006/001696
§ 371 (c)(1), (2), (4) Date: Jul. 22, 2009

(87) PCT Pub. No.: WO2006/120575
PCT Pub. Date: Nov. 16, 2006

(65) Prior Publication Data
US 2010/0062977 A1 Mar. 11, 2010

(30) Foreign Application Priority Data
May 6, 2005 (GB) .................................. 0509318.2

(51) Int. Cl.
*A61K 39/395* (2006.01)
(52) U.S. Cl. .................................................. 424/141.1
(58) Field of Classification Search .................. None
See application file for complete search history.

(56) References Cited

U.S. PATENT DOCUMENTS 6,294,167 B1 * 9/2001 Lindhofer et al. ........... 424/93.7
2003/0077273 A1 * 4/2003 Linnik et al. ................ 424/131.1

OTHER PUBLICATIONS

Sheridan C., 2006, Nature Biotechnology, 24: 475-476.*
Cibotti, et al., "Surface Molecules that Drive T Cell Development In Vitro in the Absence of Thymic Epithelium and in the Absence of Lineage-Specific Signals," *Immunity* 6(3):245-255 (1997).
Elflein, et al., "Rapid Recovery from T Lymphopenia by CD28 Superagonist Therapy," *Blood* 102(5):1764-1770 (2003).
Lin, et al., "Efficient Expansion of Regulatory T Cells In Vitro and In Vivo with CD28 Superagonist," *Eur J Immunol* 33(3):626-638 (2003).
Schmidt, et al., "Treatment and Prevention of Experimental Autoimmune Neuritis with Superagonistic CD28-Specific Monoclonal Antibodies," *J Neuroimmunology* 140(1-2):143-152 (2003).
Wack, et al., "Binding of the Hepatitus C Virus Envelope Protein E2 to CD81 Provides a Co-Stimulatory Signal for Human T Cells," *Eur J Immunol* 31(1):166-175 (2001).
Witherden, et al., "CD81 and CD28 Costimulate T Cells Through Distinct Pathways," *J Immunol* 165(4):1902-1909 (2000).
Witherden, et al., "CD81 and CD28 Costimulate T Cells Through Distinct Pathways," *FASAB J* 13(4):A627 (1999).

* cited by examiner

*Primary Examiner* — Ilia Ouspenski
(74) *Attorney, Agent, or Firm* — Kenneth M. Goldman; Leonardo Rasile; Roberta Robins

(57) ABSTRACT

A method for TCR-independent T cell activation which comprises the co-ligation of CD28 and CD81.

12 Claims, 25 Drawing Sheets

Grey: Isotype Control
Black: Anti-CCR4-PE

Top Row: Human CD45RO negative (t=0) CD8 T-cells
Bottom Row: Human CD45RO negative (t=0) CD4 T-cells Grey: Isotype Control
Black: Anti-CXCR3-FITC Red: Anti-CD28 + Anti-CD81 (CD25+CD69+ gated cells)
Blue: Anti-CD28 + isotype control (CD25+CD69- gated cells)
Green: Medium (CD25-CD69- gated cells)
Grey: PMA + Ionomycin (CD25+CD69+ gated cells)
Black Dashed: Mouse IgG1-PE isotype control

TCR-INDEPENDENT ACTIVATION OF T CELLS

This application is a §371 National Phase filing of PCT/IB2006/001696, filed May 8, 2006, which claims the benefit of GB 0509318.2, filed May 6, 2005, from which applications priority is claimed pursuant to the provisions of 35 U.S.C. §§119/120 and which applications are incorporated by reference herein in their entireties.

All documents cited herein are incorporated by reference in their entirety.

TECHNICAL FIELD

This invention is in the field of immune regulation, and in particular the activation of T cells.

BACKGROUND ART

T cells constitute about 60% of circulating blood leukocytes and play a central role in adaptive immunity. T cells recognise protein antigens complexed with MHC molecules through their T cell receptor-CD3 ("TCR/CD3") complex. Naïve T cells need additional signals provided by professional antigen presenting cells (APCs), for example, CD28-CD80/86 interactions. It is well established that the triggering of the TCR is a central event in T cell activation and that ligation of additional co-stimulatory molecules is necessary for full stimulation of T cells.

Recently, TCR-independent methods of T cell activation have been disclosed. For example, the TCR-independent CD28 signal leads the selective transcription of survival (Bcl-xL) and inflammatory (IL-8 and B cell activation factor), but not proliferative (IL-2) genes, in a NFκB-dependent manner [1]. Further, ref. 2 teaches that, in the absence of TCR ligation, CD28 stimulation induced Th2 differentiation of memory, but not of naïve CD4(+) T cells.

It is an object of the invention to provide further and improved methods for TCR-independent T cell activation.

DISCLOSURE OF THE INVENTION

It has now surprisingly been found that T cell activation can occur, in the absence of any role of the TCR/CD3 complex, by co-ligating CD28 and CD81.

CD28 is the prototypic T cell co-stimulatory molecule and binds to molecules of the B7 family expressed on APCs such as dendritic cells and activated B cells. Human CD28 is found on all CD4+ T cells and on about half of CD8+ T cells. T cell activities attributed to CD28 include prevention of anergy, induction of cytokine gene transcription, stabilization of cytokine mRNA and activation of CD8+ cytotoxic T lymphocytes. The ligands for CD28 identified as CD80(B7-1) and CD86(B7-2) are immunoglobulin superfamily monomeric transmembrane glycoproteins of 60 kd and 80 kd respectively.

CD81 is a member of the tetraspanin superfamily of proteins. It is expressed on a broad array of tissues, including T cells, hepatocytes and hematopoietic cells. CD81 is involved in a wide variety of biological processes e.g. regulation of B cell signalling, fusion of macrophages and the T cell-APC immunological synapse. CD81 is known to play an immunomodulatory role. In particular, cross-linking of CD81 enhances CD3 mediated activation of αβ and γδ T-lymphocytes and induces TCR-independent production of cytokines by γδ T cells in vitro [3,4]. CD81−/− mice showed defective immune responses to T-dependent antigens, but not to T-independent antigens of type I and II [5-7]. Reference 8 concluded that ligation of CD81 decreases the signalling threshold required to initiate TCR/CD3-mediated induction of integrated HIV-1 proviral DNA in primary CD4+ T cells. Studies have also investigated whether the presence or absence of CD81 on T cells from transgenic mice has a role in the induction of Th2 responses [9-11]. The results of the studies indicated that CD81 is important for eliciting Th2 responses against T-dependent antigens, which cause binding of the TCR. An experiment in which naïve T cells were primed in vitro against T-dependent antigens in the presence of antibodies specific for CD81 has also been described [9]. The investigators found that binding of CD81 during such priming inhibited a Th2 response against the antigen. CD81 is also known to be a receptor for hepatitis C virus (HCV) entry into cells, mediated by binding of the HCV E2 envelope protein with high affinity and species specificity [12].

CD28 and CD81 are known to co-stimulate T cells through distinct pathways [13]. It has now been found that co-ligation of the CD28 and CD81 receptors leads to a proliferative response and also to the production of cytokines. Bypassing the requirement for the TCR/CD3 allows the modulation of the adaptive immune response by an antigen-independent mechanism, thereby allowing general up-regulation of the immune response.

Thus the invention provides a method for TCR-independent T cell activation in which CD28 and CD81 are co-ligated, i.e. CD28 and CD81 are simultaneously bound on the surface of T cells.

The finding that CD28 and CD81 can be used to activate T cells is particularly useful for treating HCV infection, and can overcome the frequent failure of the immune response to clear HCV. It can also treat or prevent auto-immune phenomena that are often observed in chronic HCV infection.

Co-Ligation (Also Known as 'Co-Engagement')

CD28 and CD81 can be co-ligated by a single bi-specific ligand, or by two distinct ligands. The use of distinct ligands is preferred, and in this case the ligands will typically each be capable of stimulating T cells.

The CD28 ligand is preferably an anti-CD28 antibody, more preferably an anti-CD28 monoclonal antibody (mAb). Anti-CD28 mAbs are known in the art e.g. see references 14, 15, etc. It has been found that not all anti-CD28 antibodies can suitably activate naïve T cells in the context of the present invention. Preferred anti-CD28 antibodies are CD28 superagonists [16], which bind to a different epitope on CD28 from the natural ligand, and which can effect activation of CD28 without acting via the TCR. Reference 16 distinguishes "conventional" mAbs (TCR signalling-dependent costimulatory mAbs) and "superagonistic" mAbs (capable of inducing the full activation of primary resting T cells in the absence of TCR ligation both in vitro and in vivo; or "autonomously mitogenic CD28-specific antibody"). Preferred superagonistic antibodies are those that can compete for CD28 binding with the JJ316 antibody disclosed in ref. 16 and/or that bind to the C"D loop of CD28 (e.g. within amino acids 37-66 of the native rat CD28) rather than to the B7 binding site.

It is preferred that a CD28 superagonist is not used in vivo in a patient. Instead, it is preferred to remove T cells from a patient, treat the T cells with the CD28 superagonist ex vivo and then retransplant the treated T cells into the patient. Thus, a method of the invention may be performed on a T cell ex vivo.

Alternatively, or additionally, the CD28 ligand may be based on a natural CD28 ligand, such as CD80 or CD86 (also known as B7-1 and B7-2). Thus the CD28 ligand may be a soluble form of one of these receptors e.g. lacking at least the transmembrane domain. Soluble forms of B7-1 are known e.g. see refs. 17-19. Soluble forms of CD86 exist naturally, and have also been prepared artificially e.g. see refs. 19-22

The CD81 ligand may be an anti-CD81 antibody, such as a mAb. One such mAb is MG81NA, a mouse monoclonal antibody which is also known as MG81NB (see below). Rather than using an anti-CD81 antibody, however, it is preferred to engage CD81 using the HCV E2 protein, or a protein comprising an E2 fragment that retains the CD81-binding activity of E2. In general, the E2 protein will not be provided endogenously during therapy, but will be present in a patient as a consequence of HCV infection. Provision of a CD28 ligand thus permits co-ligation on T cells that are bound to HCV virions, thereby activating them in a TCR-independent manner. By using the endogenous infection-specific ligand, rather than a general ligand, activation is restricted to infected cells, thereby avoiding any deleterious (e.g. immunopathological) effects of non-specific systemic T cell activation.

Co-ligation may be carried out in vivo or in vitro. The in vitro methods can be used for investigation, testing and modelling, whereas the in vivo methods can be used for therapy. In in vitro methods, the CD28 and CD81 ligands may each independently be soluble or bound to a solid phase. In in vivo methods, the CD28 and CD81 ligands will be used in soluble form.

In a preferred in vivo embodiment, as described above, CD81 is ligated by E2 protein arising from the existing HCV infection. In this preferred embodiment, a method of therapy involves administering a CD28 ligand to a patient infected with HCV. In an alternative in vivo embodiment, the CD28 ligand is endogenous, and immune modulation is effected by administering an exogenous CD81 ligand.

In a preferred in vitro embodiment, the method comprises ligating CD28 in the soluble phase (e.g. using a soluble anti-CD28 antibody), and ligating CD81 on a solid phase (e.g. using an immobilised anti-CD81 antibody). In a particularly preferred in vitro embodiment, the method comprises the steps of: (a) taking a vessel in which E2 has been immobilised to the surface of the well using anti-E2 antibodies and from which any excess E2 still in solution has been washed out; (b) adding a culture medium containing the T cells to be activated to the vessel of step (a); and (c) co-ligating CD28 and CD81 using anti-CD28 antibodies present in the culture medium and the bound E2.

Preferably, the methods of the invention, whether in vitro or in vivo, are used to activate αβ T cells. The methods may additionally or alternatively be used to activate γδ T cells.

The invention also provides T cells that have been activated by using the methods of the invention. The activation of T cells leads to their proliferation and/or differentiation.

The invention relates to methods for the TCR-independent activation of CD4+ T cells and CD8+ T cells. Preferably, the T cells to be activated are CD4+ T cells.

T-helper 1 (Th1) and T-helper 2 (Th2) cells arise from differentiation of naive CD4+ T cells. They have a crucial role in balancing the immune response. One important feature of these cells is that each subset can cross-regulate the other mainly by secretion of soluble factors (cytokines).

It is possible to determine whether a T cell has a Th1 profile or a Th2 profile by looking at which markers are being produced by the T cell and the levels of these markers. The markers which may be examined include cytokines produced by the cell, cytokine receptors and chemokine receptors expressed by the cell and transcription factors. The skilled person can determine whether a T cell has a Th1 profile or a Th2 profile by comparing the markers produced by the cell to the markers produced by a control cell. Th1 and Th2 responses are discussed extensively in the art [23-25].

For example, Th1 T cells release cytokines such as IL-2 and interferon-γ. Other examples of Th1 markers that are secreted or expressed (as appropriate) by T cells which have a Th1 profile are IL-3 and TNF-α (cytokines); IL-12Rβ2, IL18R (cytokine receptors); CXCR3, CCR5 (chemokine receptors); and tim3, stat4, T-bet (transcription factors). As used herein, the term "Th1 markers" refers to the markers that are expressed or secreted by Th1 cells. A T cell having a Th1 profile secretes or expresses at least one Th1 marker and preferably secretes or expresses at least two, three, four, five or more Th1 markers. A T cell having a Th1 profile is said to generate a Th1 response.

For example, Th2 T cells release cytokines such as IL-4. Other examples of Th2 markers that are secreted or expressed (as appropriate) by T cells which have a Th2 profile are IL-13, IL-5 (cytokines); IL1R, IFN-γR (cytokine receptors); CCR4, CCR8 (chemokine receptors); and tim1, stat6, gata3 (transcription factors). As used herein, the term "Th2 markers" refers to the markers that are expressed or secreted by Th2 cells. Preferably, a T cell having a Th2 profile secretes or expresses at least one Th2 marker and preferably secretes or expresses at least two, three, four, five or more Th2 markers. A T cell having a Th2 profile is said to generate a Th2 response.

In certain embodiments, an activated T cell of the invention may have at least a Th1 profile or at least a Th2 profile. By the expressions "at least a Th1 profile" or "at least a Th2 profile" is meant that the T cell may have a Th1 or Th2 profile respectively, as described above, but may additionally secrete or express one or more other markers. If the T cell has at least a Th1 profile, these one or more other markers are preferably not Th2 markers, or any Th2 markers that are produced are produced at a level which is lower than for Th2 cells. If the T cell has at least a Th2 profile, these one or more other markers are preferably not Th1 markers, or any Th1 markers that are produced are produced at a level which is lower than for Th1 cells.

In mouse models, Th1 cells induce production of IgG2a by B-cells, whereas Th2 cells induce production of IgE and IgG1. However, the same is not true for humans. Thus, in mice, antibody isotype can be examined to test whether a Th1 or Th2 profile has been established.

Differentiated CD8+ T cells are classified as T-cytotoxic 1 (Tc1) and 2 (Tc2) cells instead of Th1 and Th2 cells. A similar pattern of cytokine differentiation as has been observed for CD4 T cells has been observed for CD8 T cells. The skilled person can determine whether a CD8+ T cell has a Tc1 or a Tc2 profile using standard techniques in the art.

The term "type 1 cell(s)" or "type 1 T cell(s)" is used herein to refer to Th1 or Tc1 cells. The term "type 2 cell(s)" or "type 2 T cell(s)" is used herein to refer to Th2 or Tc2 cells.

Initial experiments have suggested that total T cells (i.e., T cell populations comprising both naïve T cells and effector T cells, see FIGS. 1-7) and naïve T cells (see FIG. 8) activated by a method of the invention produce high levels of IFN-γ and do not produce IL-4. The production of TNF-α has also been observed. Thus the T cells in some embodiments of the present invention preferably have at least a Th1 profile. This contrasts with T cells activated by the prior art CD28-dependent TCR-independent methods, which have exclusively a Th2 profile. These initial experiments used ELISA assays to monitor the production of TNF-α and IFN-γ following co-ligation of CD28 and CD81 mainly on total human T cells. TNF-α and IFN-γ are characteristic of Th1 responses. No other cytokines were detected as no other cytokines were assayed. The T cells of this embodiment, which have a Th1 profile, are particularly useful for treating bacterial infections.

In other embodiments of the invention, the activated T cells of the present invention have at least a Th2 profile. TNF-α and IFN-γ are not the only cytokines that are secreted by the T cells. At least 8 more cytokines can be detected (see FIGS. 16-26).

The invention also provides a method for the TCR-independent activation of naïve T cells. Preferably, the naïve T cells are human T cells. The inventors have found that co-ligation of CD28 and CD81 enables naïve T cells to be activated. This is surprising in light of the teaching that, in the absence of TCR ligation, CD28 stimulation induces Th2 differentiation of memory, but not of naïve CD4(+) T cells [2]. The present inventors surprisingly found that, by co-ligation of CD81 in addition to CD28, naïve T cells could be activated. Preferably, the naïve T cells activated by a method of the invention are induced to differentiate into type 2 cells. Preferably, the type 2 cells are Th2 cells. Alternatively, the type 2 cells may be Tc2 cells.

The invention also provides a method for activating type 2 cells, i.e., a method for activating T cells that are already differentiated to type 2 cells. Preferably, the method according to this aspect of the invention does not also activate type 1 cells and/or type 0 cells (type 0 T cells produce both IFN-γ and IL-4). This aspect of the invention preferably activates type 2 cells to proliferate.

The invention further comprises a method for switching a differentiated effector T cell to a type 2 T cell. According to this embodiment, the method is preferably for switching type 1 cells to type 2 cells. Preferably, the type 1 and type 2 cells are Th1 cells and Th2 cells, respectively. Alternatively, the method is for switching type 0 cells to type 2 cells. The switching of type 1 to type 2 cells is useful where an individual has a dangerous type 1 response, or a lack of a useful type 2 response. Thus, the method of the invention may be used for treating an individual that exhibits a dangerous type 1 response, or a lack of a useful type 2 response, or both. Preferably, the T cells are removed from the patient and potentially damaging cells are identified based on antigen specificity of type 1 phenotype. These potentially damaging cells are then stimulated ex vivo to co-ligate CD28 and CD81, preferably using anti-CD28 plus anti-CD81. Following verification that the cells have switched to type 2 cells, the cells may then be reintroduced into the bloodstream of patients. Alternatively, co-ligation may be performed in vivo.

The method for switching type 1 cells to type 2 cells can be used as a platform to develop a therapy against autoimmune diseases which are due to autoimmune reactions mediated by type 1 cells (preferably by Th1 cells). In particular, the invention provides a method for treating Hashimoto's thyroiditis, multiple sclerosis or insulin-dependent diabetes mellitus.

For example, studies performed on mice affected by experimental encephalomyelitis (an animal model of multiple sclerosis) have shown that transfer into healthy mice of Th1 clones specific for self-antigens from the nervous system results in the transfer of the autoimmune disease to the healthy mice. In contrast, transfer of Th2 clones not only did not transfer the disease, but also protected the mice from induction of the disease when commonly-used experimental inducing methods are used [26-31]. Thus, the provision of a method for switching type 1 T cells to type 2 T cells has significant therapeutic advantages.

In a preferred embodiment, the T cells activated by a method of the invention are characterised in that CD69, CD25 and CD38 markers are up-regulated.

The T cells to be activated by a method of the invention are preferably human T cells.

Therapy

The TCR-independent activated T cells of the present invention, and one or both of the CD28 and CD81 ligands, are of use for the treatment of diseases which are treatable by the general upregulation of the immune system. In particular, the invention is of use for the treatment of a disease in which CD81-binding is involved.

Preferably, the disease is an intracellular disease, and is more preferably a viral infection. The disease is preferably one which responds to a Th1 cytokine profile.

It is known that the binding of HCV E2 to CD81 inhibits natural killer (NK) cell activity in vitro. However, NK cells have recently been discovered which also express CD28. Thus the methods of the invention can be used to overcome the negative effect of CD81 ligation on NK cells. This advantageously provides a method for treating diseases which involve the inhibition of NK cells so as to overcome this inhibition.

The methods of the invention are particularly useful for treating HCV infections, including chronic HCV infections.

Viral clearance during acute infection is related to CD4+ and CD8+ T cell responses that are multispecific, strong and of long duration (years). Viral clearance comprises a "stunned" CD8+ initial phase followed by a IFN-γ producing switch to activated CD4+ HCV-specific T cells, which produce IFN-γ from self-clearing individuals. Anti-HCV antibodies usually develop 2 to 8 months after acute infection. Mature CD83+ dendritic cells are detected in the liver of chronically infected patients. Alanine aminotransferase (ALT) is an enzyme produced within the cells of the liver and is used to determine whether the liver is damaged or diseased. A high level of ALT often correlates with a high level of liver damage. High levels of ALT are associated with a Tc2 response, whereas low levels of ALT are associated with a Tc1 response. IFN-α is thought to promote HCV-specific immunity.

The invention also provides a pharmaceutical composition comprising a CD28 ligand. The composition can be used to treat the conditions described above. The pharmaceutical composition may also comprise a CD81 ligand but, preferably, the CD28 ligand is the sole active ingredient.

The use of monoclonal antibodies as the active ingredient of pharmaceuticals is now widespread, including the products Herceptin™ (trastuzumab), Rituxan™, Campath™, Remicade™, ReoPro™, Mylotarg™, Zevalin™, Omalizumab, Synagis™ (Palivizumab), Zenapax™ (daclizumab), etc. These include antibodies that recognise human self-antigens (e.g. Herceptin™ recognises the Her2 marker) and antibodies that recognise pathogenic antigens (e.g. Synagis™ recognises an antigen from respiratory syncytial virus).

The pharmaceutical composition may also include, or may be co-administered with, a further active agent, such as a cytokine (e.g. an interferon or an interleukin) or a vaccine (e.g. a HCV vaccine).

The invention provides a method of treating a patient, comprising a step of administering a CD28 ligand to the patient, optionally in combination with a CD81 ligand. Preferably, the individual is infected with HCV. As described above, the CD28 ligand may be administered in combination with a further active agent, and this further agent may be administered simultaneously with or separately from the CD28 ligand i.e. they are for separate simultaneous or sequential use.

The invention also provides the use of a CD28 ligand in the manufacture of a medicament for the treatment of a disease.

The CD28 ligand may be used in combination with a CD81 ligand and/or a further active agent, as described above. The medicament is particularly suitable for treating patients having a HCV infection.

The CD28 ligand and further active agent may be provided as separate components in a kit.

Pharmaceutical compositions of the invention include one or more pharmaceutical carrier(s) and/or excipient(s). A thorough discussion of pharmaceutically acceptable carriers is available in ref. 32.

To control tonicity, it is preferred to include a physiological salt, such as a sodium salt. Sodium chloride (NaCl) is preferred, which may be present at between 1 and 20 mg/ml.

Compositions will generally have an osmolality of between 200 mOsm/kg and 400 mOsm/kg, preferably between 240-360 mOsm/kg, and will more preferably fall within the range of 290-300 mOsm/kg.

Compositions of the invention may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of a composition of the invention will generally be between 5.0 and 7.5, and more typically between 5.0 and 6.0 for optimum stability, or between 6.0 and 7.0. The process of the invention may therefore include a step of adjusting the pH of the bulk vaccine prior to packaging.

Compositions of the invention are preferably sterile.

Compositions of the invention are preferably non-pyrogenic e.g. containing <1 EU (endotoxin unit, a standard measure) per dose, and preferably <0.1 EU per dose.

Compositions of the invention are preferably gluten free.

Compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition, like Synagis™ and Herceptin™, for reconstitution with sterile water containing a preservative). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. For example, a lyophilised antibody can be provided in kit form with sterile water or a sterile buffer. Compositions of the invention will generally be in aqueous form.

Compositions of the invention may be administered to patients in 0.5 ml doses. References to 0.5 ml doses will be understood to include normal variance e.g. 0.5 ml±0.05 ml.

Pharmaceutical compositions include an effective amount of one or more ligands i.e. an amount sufficient to treat, ameliorate, or prevent a desired disease or condition, or to exhibit a detectable therapeutic effect. Therapeutic effects also include reduction in physical symptoms. The precise effective amount for any particular patient will depend upon their size and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.01 mg/kg to about 50 mg/kg, or about 0.05 mg/kg to about 10 mg/kg. Known antibody-based pharmaceuticals provide guidance in this respect e.g. Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; etc.

The invention is particularly suitable for therapy in human patients.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid. Compositions of the invention can be administered by intramuscular injection e.g. into the arm or leg.

Where the active ingredient in the composition comprises an antibody molecule, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

CD3

The invention is described above in terms of co-ligation of CD28 and CD81. In alternative methods of the invention, CD3 and CD81 are co-ligated. The definitions above can be modified accordingly.

CD28 Superagonist

The invention is described above in terms of co-ligation of CD28 and CD81. In alternative methods of the invention, a CD28 superagonist can be used in the absence of CD81 ligation. The definitions above can be modified accordingly.

Ligation of CD28 by CD28 superagonists is particularly useful for TCR-independent methods for switching a differentiated effector T cell to a type 2 T cell. A method according to this embodiment is preferably for switching type 1 T cells to type 2 T cells. Preferably the type 1 and type 2 T cells are Th1 and Th2 cells, respectively. In this alternative aspect, the CD28 superagonist may be used in the absence of an agent which co-ligates CD81.

The method for switching type 1 cells to type 2 cells can be used as a platform to develop a therapy against autoimmune diseases which are due to autoimmune reactions mediated by type 1 cells (preferably by Th1 cells). In particular, the invention provides a method for treating Hashimoto's thyroiditis, multiple sclerosis or insulin-dependent diabetes mellitus comprising use of a CD28 superagonist to ligate CD28.

The CD28 superagonist, when used alone, is not stimulatory on human naïve cells but is an important mitogen for effector memory cells. Thus, the T cells for use in the method preferably do not comprise just naïve T cells. For example, the T cells for use in the method preferably comprise a total T cell population (comprising both naïve and effector T cells) or effector T cells only.

Further, it is preferred that the CD28 superagonist is not used in vivo in a patient. Instead, it is preferred to remove T cells from a patient, treat the T cells with the CD28 superagonist ex vivo and then retransplant the T cells into the patient. Thus, this aspect of the invention provides a method that can be performed ex vivo.

Antibodies

Where the invention uses an antibody, it is preferably a monoclonal antibody. The term 'monoclonal antibody' includes any of the various artificial antibodies and antibody-derived proteins which are available e.g. human antibodies, chimeric antibodies, humanized antibodies, single-domain antibodies, single-chain Fv (scFV) antibodies, monoclonal oligobodies, dimeric or trimeric antibody fragments or constructs, minibodies, etc., or functional fragments thereof which bind to the antigen in question.

In a natural antibody molecule, there are two heavy chains and two light chains. Each heavy chain and each light chain has at its N-terminal end a variable domain. Each variable domain is composed of four framework regions (FRs) alternating with three complementarity determining regions (CDRs). The residues in the variable domains are conventionally numbered according to a system devised by Kabat et al. [33]. The Kabat residue designations do not always correspond directly with the linear numbering of the amino acid residues and the linear amino acid sequence may contain fewer or additional amino acids than in the strict Kabat numbering. This may correspond to a shortening of, or insertion into, a structural component, whether framework or CDR, of the basic variable domain structure.

Some antibodies described herein are non-human (e.g. murine, rabbit). To avoid a non-specific anti-xeno immune response in humans, the antibodies of the invention are preferably humanized or chimeric. [e.g. refs. 34 & 35]. As an alternative, fully-human antibodies may be used.

In chimeric antibodies, non-human constant regions are substituted by human constant regions but variable regions remain non-human. Humanized antibodies may be achieved by a variety of methods including, for example: (1) grafting complementarity determining regions (CDRs) from the non-human variable region onto a human framework ("CDR-grafting"), with the optional additional transfer of one or more framework residues from the non-human antibody ("humanizing"); (2) transplanting entire non-human variable domains, but "cloaking" them with a human-like surface by replacement of surface residues ("veneering"). In the present invention, humanized antibodies include those obtained by CDR-grafting, humanizing, and veneering of the variable regions. [e.g. refs. 36 to 42].

Humanized or fully-human antibodies can also be produced using transgenic animals that are engineered to contain human immunoglobulin loci. For example, ref. 43 discloses transgenic animals having a human Ig locus wherein the animals do not produce functional endogenous immunoglobulins due to the inactivation of endogenous heavy and light chain loci. Ref. 44 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. Ref. 45 discloses the use of the Cre/Lox system to modify the immunoglobulin locus in a mammal, such as to replace all or a portion of the constant or variable region to form a modified antibody molecule. Ref. 46 discloses non-human mammalian hosts having inactivated endogenous Ig loci and functional human Ig loci. Ref. 47 discloses methods of making transgenic mice in which the mice lack endogenous heavy chains, and express an exogenous immunoglobulin locus comprising one or more xenogeneic constant regions.

Antibodies naturally have two separate chains, however, it is preferred to use a single chain antibody ("sFv" or "scFv") in which the light and heavy chain variable domains are joined by a linker to give a single polypeptide chain. Kits for preparing scFv's are available off-the-shelf, and anti-ligand scFvs are preferred second sequences for use with the invention. Single domain antibodies can also be obtained from camelids or sharks [48], or by camelisation [49].

A sFv polypeptide is a covalently linked $V_H$-$V_L$ heterodimer which is expressed from a gene fusion including $V_H$- and $V_L$-encoding genes linked by a peptide-encoding linker [50]. A number of methods have been described to discern and develop chemical structures (linkers) for converting the naturally aggregated, but chemically separated, light and heavy polypeptide chains from an antibody V region into an sFv molecule which will fold into a three dimensional structure substantially similar to the structure of an antigen-binding site. See, e.g., refs. 51-53. The sFv molecules may be produced using methods described in the art. Design criteria include determining the appropriate length to span the distance between the C-terminus of one chain and the N-terminus of the other, wherein the linker is generally formed from small hydrophilic amino acid residues that do not coil or form secondary structures. Such methods have been described in the art [e.g. refs. 51-53]. Suitable linkers generally comprise polypeptide chains of alternating sets of glycine and serine residues, and may include glutamic acid and lysine residues inserted to enhance solubility.

"Mini-antibodies" or "minibodies" will also find use with the present invention Minibodies are sFv polypeptide chains which include oligomerization domains at their C-termini, separated from the sFv by a hinge region [54]. The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g [54], [55].

"Oligobodies" will also find use with the present invention. Oligobodies are synthetic antibodies. The specificity of these reagents has been demonstrated by Western blot analysis and immunohistochemistry. They have some desirable properties, namely that as their production is independent of the immune system, they can be prepared in a few days and there is no need for a purified target protein [56]. Oligobodies are made by recombinant methods known in the art [57].

Antibodies are produced using techniques well known to those of skill in the art [e.g. refs. 58-63]. Monoclonal antibodies are generally prepared using the method of Kohler & Milstein (1975) [64], or a modification thereof. Typically, a mouse or rat is immunized as described above. Rabbits may also be used. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine aminopterin thymidine medium, 'HAT'). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

Where the invention refers to antibodies that have two chains (heavy and light), the invention also encompasses where appropriate the individual chains separately from each other.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

BRIEF DESCRIPTION OF DRAWINGS

FIG. 11 shows the results from engagement of CD81 with soluble anti-CD81 mAb with or without co-ligation of CD3 on T cells.

MODES FOR CARRYING OUT THE INVENTION

Generation of mAbs Specific for Human CD81-LEL.

BALB/c mice were immunized 3 times intraperitoneally with 10 μg/dose of recombinant fusion protein expressing the large extra-cellular loop (LEL) of human CD81 fused with thireodoxin (TRX-LEL CD81) [12] and MF59 (Chiron) adjuvant. One week after last immunization spleen cells were fused with X63Ag8.653 (ATCC) myeloma cells, culture supernatants were analyzed, and positive hybridoma were cloned by limiting dilution in Terazaki plates (Robbins Scientific). The human T cell lymphoma line (MOLT-4) (ATCC) expressing CD81 on the surface, was used to screen supernatant for the antibody capacity to bind CD81 and/or to inhibit the binding of HCV-E2 to CD81. Binding assays were performed by incubating MOLT-4 cells for 30 minutes at 4° C. with the culture supernatants and antibody binding was detected using a goat anti-mouse PE conjugate (Jackson Immunoresearch). Inhibition assays were performed by pre-incubating cells with culture supernatants, after 30 minutes biotinylated HCV-E2 was added and cells were stained with PE-streptavidin (Southern Biotechnology). Samples were processed using FACSCalibur flow cytometer and data were analyzed by CELLQuest software.

Monoclonal antibody MG81NA (an anti-CD81 antibody having an IgG1 isotype, [65-67]) was selected for its ability to bind CD81 and to inhibit the binding of HCV-E2 to CD81 on MOLT cells and PBMCs.

Co-Ligation of CD28 and CD81

Human T cells were purified by immunomagnetic cell sorting (purity 98%) and cultured in 96 well flat bottomed plates for tissue culture for about 72 hours. At day 2, cells were pulsed with 1 μCi/well of $^3$H-Thymidine and incubated overnight. Cells were treated using the following mAbs at the concentrations shown in FIG. 1: MG81NA coated on plastic either alone or in combination with soluble anti-human CD28 (ANC28.1/5D10, murine IgG1κ; Ancell, catalog 177-020). The anti-CD3 antibody TR66 (ATCC; [68]) coated on plastic was used as a positive control.

Figure 1:
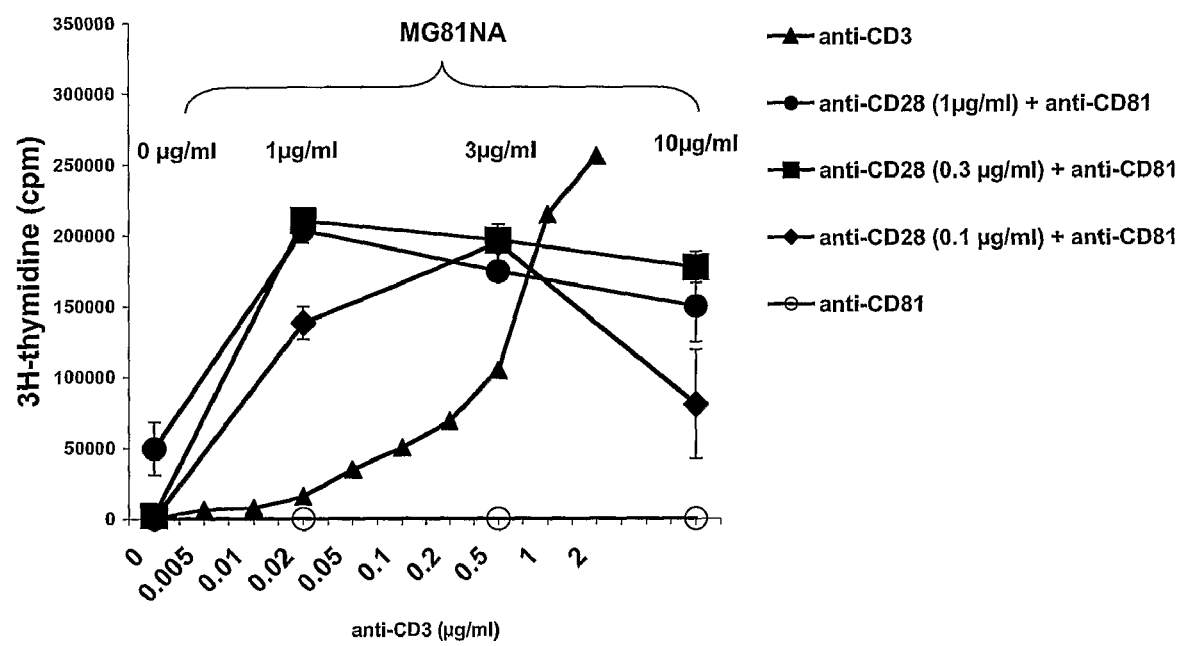
FIG. 1 shows the results of a proliferation assay for human T cells activated by a combination of soluble anti-CD28 mAb and solid-phase anti-CD81.

The results shown in FIG. 1 indicate that purified human T cells can be activated by a combination of soluble anti-CD28 mAbs and solid-phase anti-CD81. The results show that in the presence of the CD81 ligand, no proliferation occurs unless CD28 is also present. The results also indicate that the level of T cell proliferation is dependent on the dose of CD28 ligand—a higher dose leading to greater proliferation.

Figure 2:
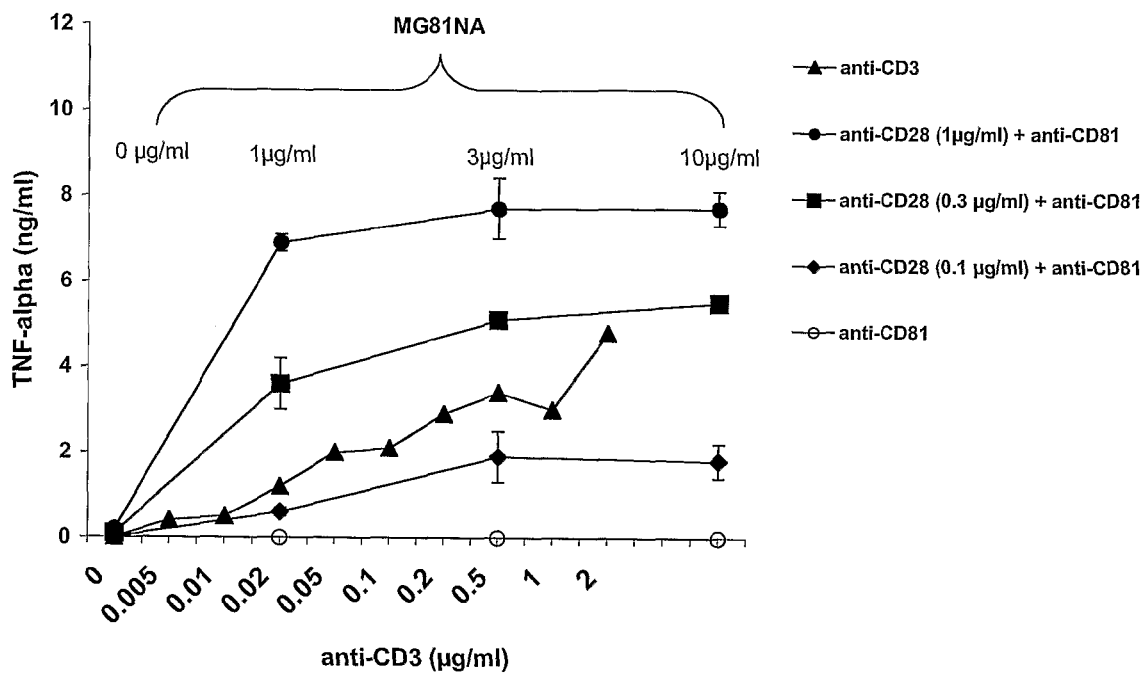
FIG. 2 shows the levels of TNFα produced by human T cells activated by a combination of soluble anti-CD28 mAb and solid-phase anti-CD81.
Figure 3:
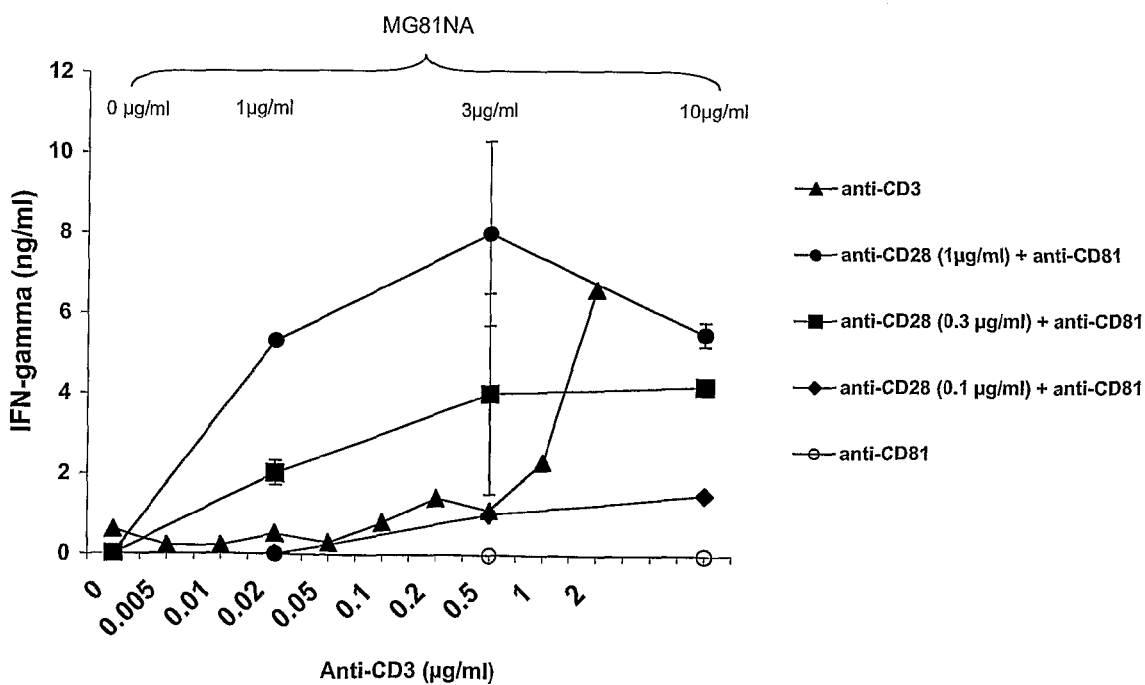
FIG. 3 shows the levels of IFNγ produced by human T cells activated by a combination of soluble anti-CD28 mAb and solid-phase anti-CD81.

Further T cells were purified and cultured as described above. The results shown in FIGS. 2 and 3 are relative to an ELISA performed on the culture supernatant taken after 48 hours of culture. Levels of TNFα were measured in FIG. 2 and levels of IFNγ were measured in FIG. 3. The results confirm that purified human T cells can be activated by a combination of soluble anti-CD28 mAbs and solid-phase anti-CD81. The results show that in the presence of the CD81 ligand, no cytokine production occurs unless CD28 is also present. The results also indicate that the level of cytokine production is dependent on the dose of CD28 ligand—a higher dose leading to a higher level of production.

HCV E2 and Anti-CD28 Monoclonal Antibodies 96 well culture plates were coated with anti E2 mAb (291A2, Chiron Corp.; [12]) at 10 μg/ml. These were then washed and incubated with recombinant HCV protein E2 at 37° C. for 1 hour. Finally, plates were washed and filled with culture medium. These plates were used to culture human T cells purified by immunomagnetic cell sorting for about 72 hours. Cells were treated with soluble anti-human CD28 at the concentrations indicated in FIG. 4. After 48 hours of culture, cells were pulsed with 1 μCi/well of $^3$H-Thymidine, incubated overnight and harvested the following day.

Figure 4:
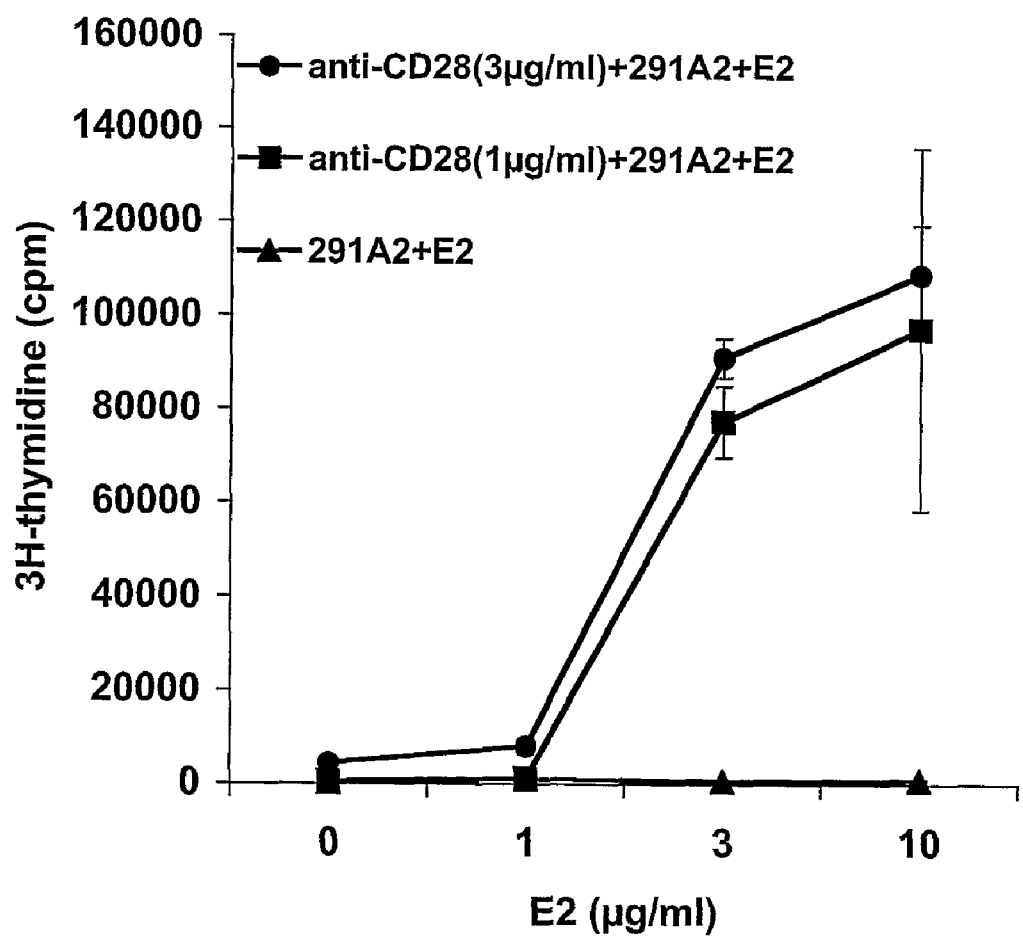
FIG. 4 shows the results of a proliferation assay for human T cells activated with HCV E2 and soluble anti-CD28 mAb.

The results shown in FIG. 4 indicate that the HCV envelope proteins synergise with anti-CD28 mAbs to induce human T cells to proliferate and secrete cytokines. The results also indicate that the level of T cell proliferation is dependent on the dose of CD28 ligand—a higher dose leading to greater proliferation.

Figure 5:
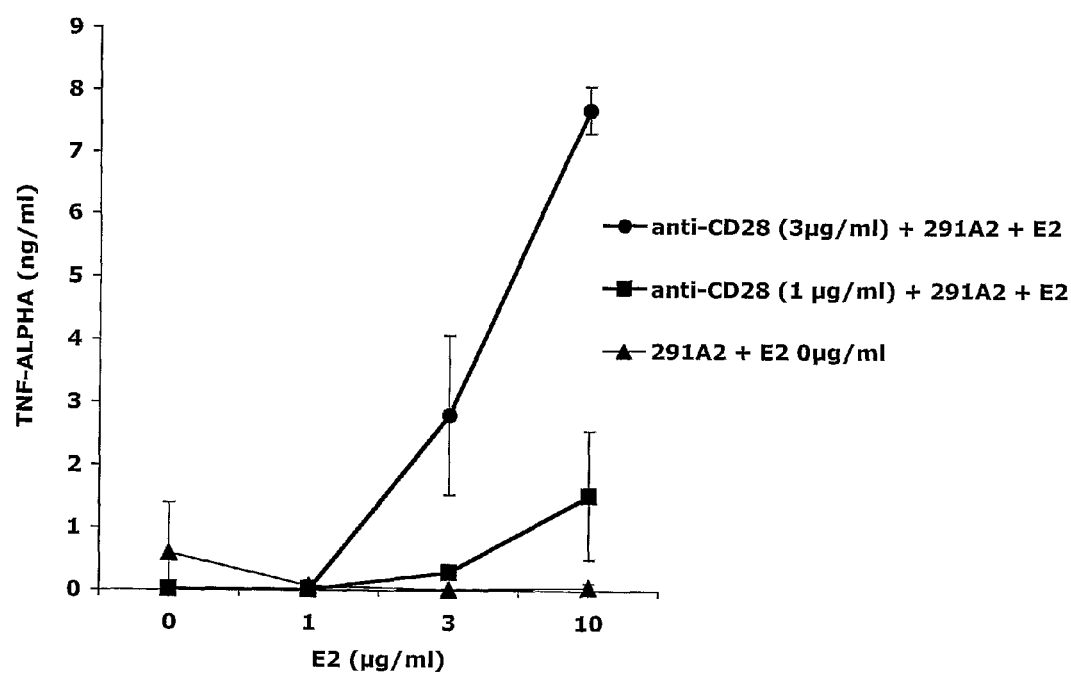
FIG. 5 shows the levels of TNFα produced by human T cells activated by a combination of soluble anti-CD28 mAb and HCV E2.
Figure 6:
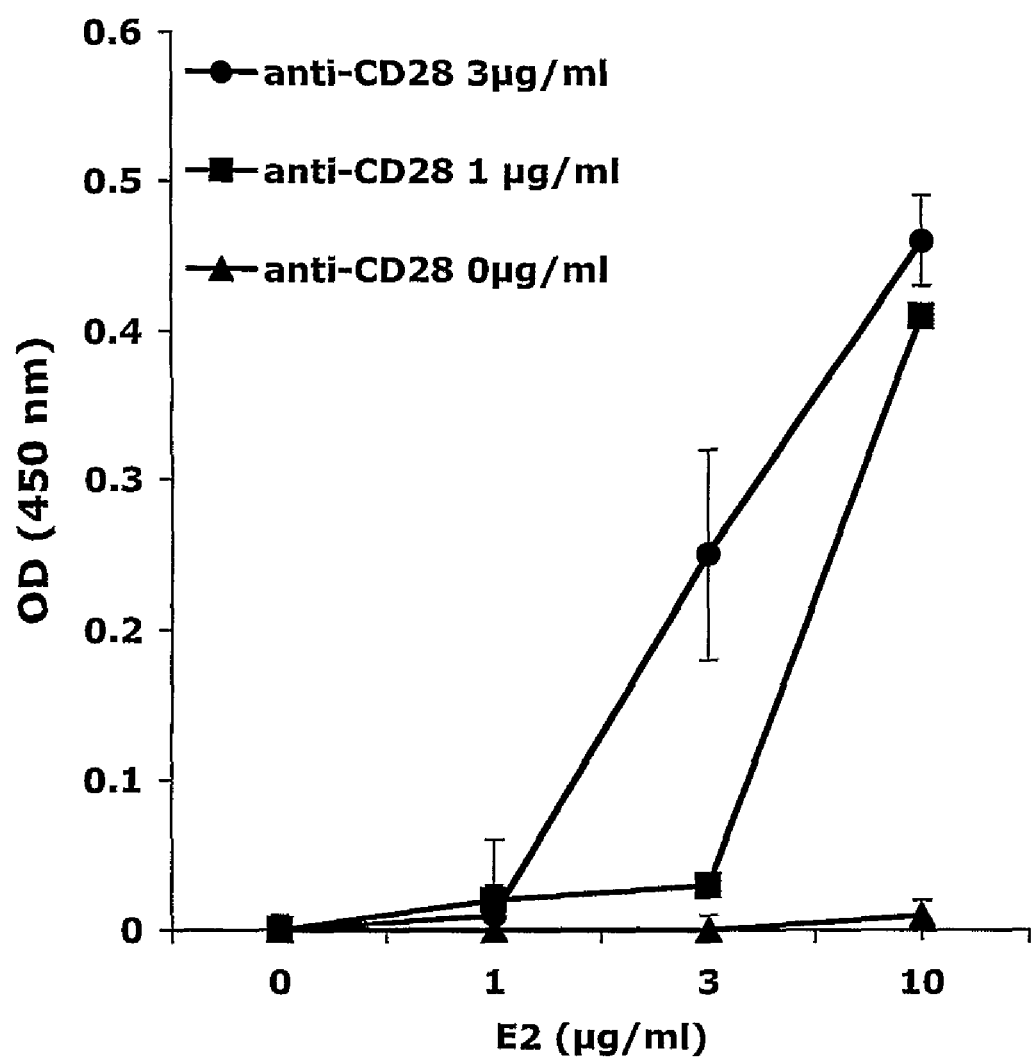
FIG. 6 shows the levels of IFNγ produced by human T cells activated by a combination of soluble anti-CD28 mAb and HCV E2.

Further T cells were purified and cultured as described above. The results shown in FIGS. 5 and 6 are shown relative to an ELISA performed on the culture supernatant taken after 48 hours of culture. Levels of TNFα were measured in FIG. 5 and levels of IFNγ were measured in FIG. 6.

The results in FIGS. 5 and 6 show that the HCV envelope proteins synergise with anti-CD28 mAbs to induce human T cells to proliferate and secrete cytokines. The results show that in the presence of the CD81 ligand, no cytokine production occurs unless CD28 is also present. The results also indicate that the level of cytokine production is dependent on the dose of CD28 ligand—a higher dose leading to a higher level of production.

Cytokines do not Synergise with Anti-CD81 Antibodies

Human PBMCs were cultured for about 72 hours in the presence of either recombinant human IL-2 or TNF-α plus MG81NA coated onto plastic. After 48 hrs, cells were pulsed with 1 μCi/well of $^3$H-thymidine, left incubating overnight and then harvested.

Figure 7A:
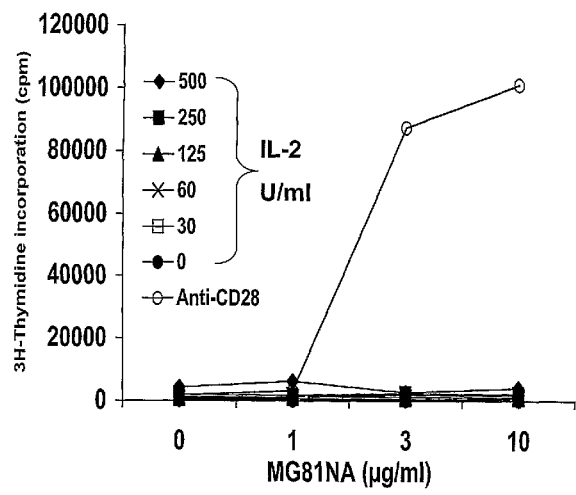
FIG. 7 shows the results of proliferation assays for human PBMCs activated with solid-phase anti-CD81 mAb (MG81NA) in the presence of recombinant human IL-2 or TNFα.
Figure 7B:
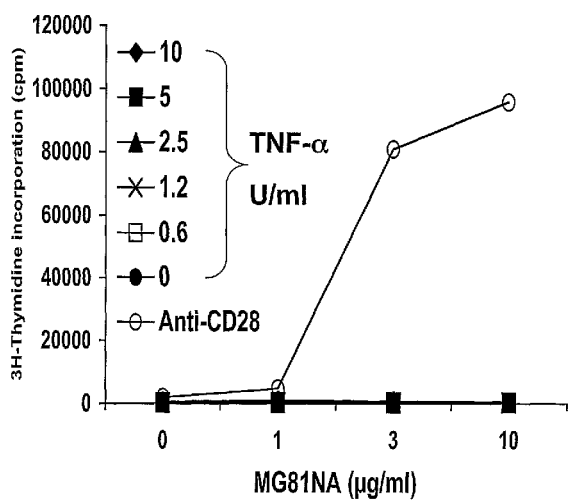

The results shown in FIG. 7 indicate that exogenous cytokines do not synergise with solid-phase anti-CD81 mAbs to induce activation of human T cells.

Figure 8A:
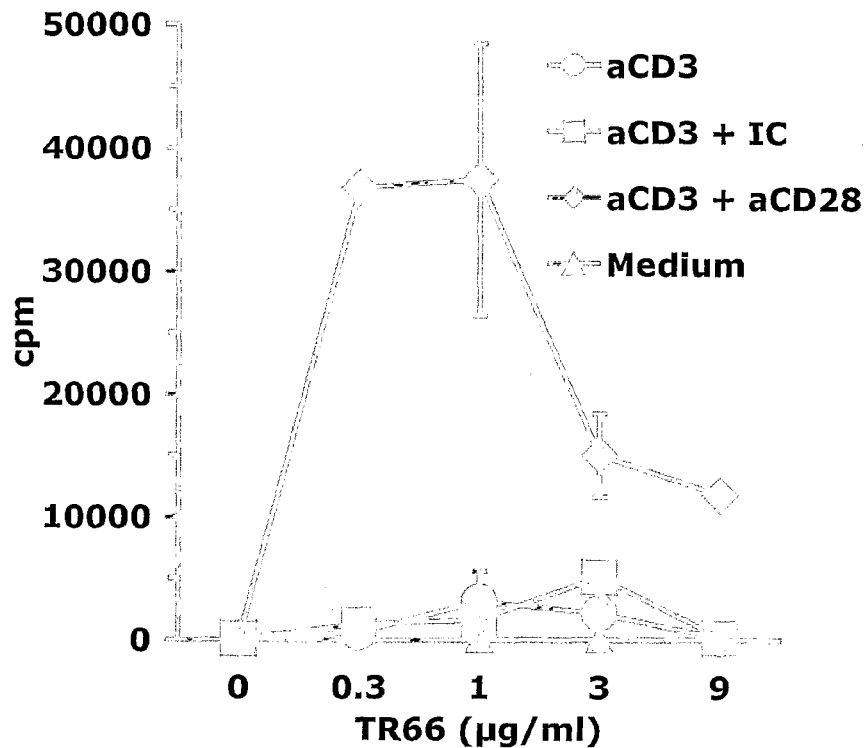
FIG. 8 shows the results of proliferation assays for human CD4+CD8−CD45RO− T cells activated by ligation of CD28 and CD81.
Figure 8B:
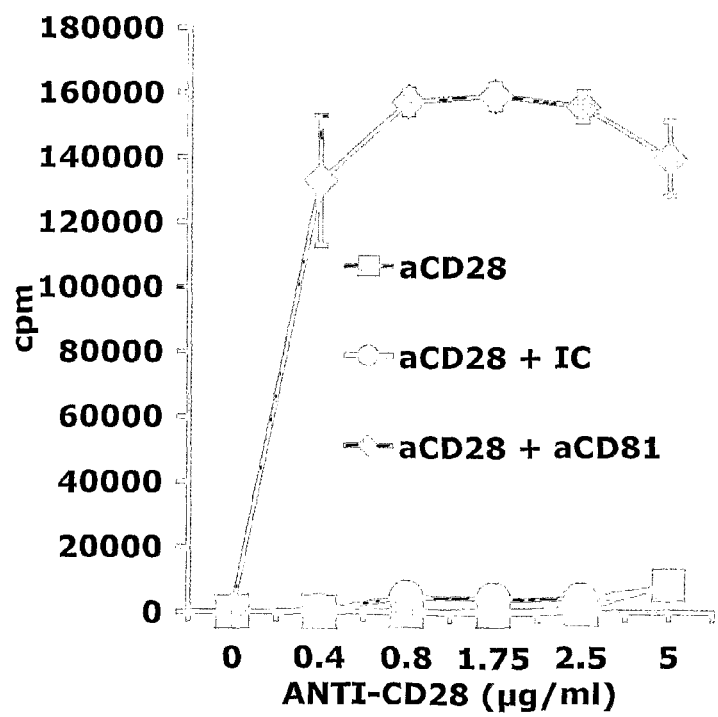

CD4+CD8−CD45RO−human T-cells were purified by immunomagnetic cell sorting. Cells were cultured under the stimuli indicated above. At day 5, cells were pulsed with $^3$H-thymidine and then their proliferation was measured. The results shown in FIG. 8 indicate that synergy between the ligation of CD28 and CD81 exerts a potent activatory signal on human naïve CD4+ T cells.

Upregulation of Cell Surface Markers

Figure 9A:
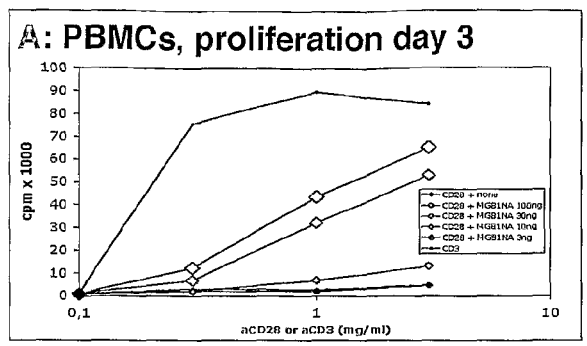
FIG. 9 shows T cell proliferation assays. Total PBMCs (FIGS. 9a and b)), PHA lines (FIG. 9c), and pure T cells (FIG. 9d) were incubated with the indicated mAbs for 3-5 days, and proliferation was measured by 3H-thymidine incorporation (FIGS. 9a, c), d)) or by CFSE (carboxyfluorescein diacetate succinimidyl ester) dilution (FIG. 9d)
Figure 9B:
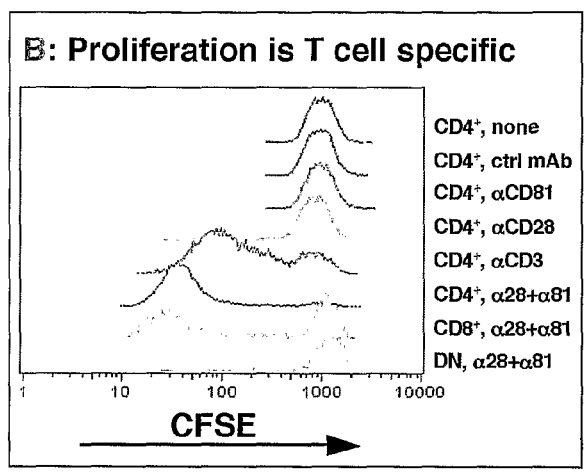

T cell proliferation: Total PBMCs (FIG. 9a, b), PHA lines (FIG. 9c) or pure T cells were incubated with the indicated mAbs (see FIG. 9) for 3-5d, and T cell proliferation was measured by 3H-thymidine incorporation (FIG. 9a, c, d), or by CFSE dilution (FIG. 9b).

Figure 10A:
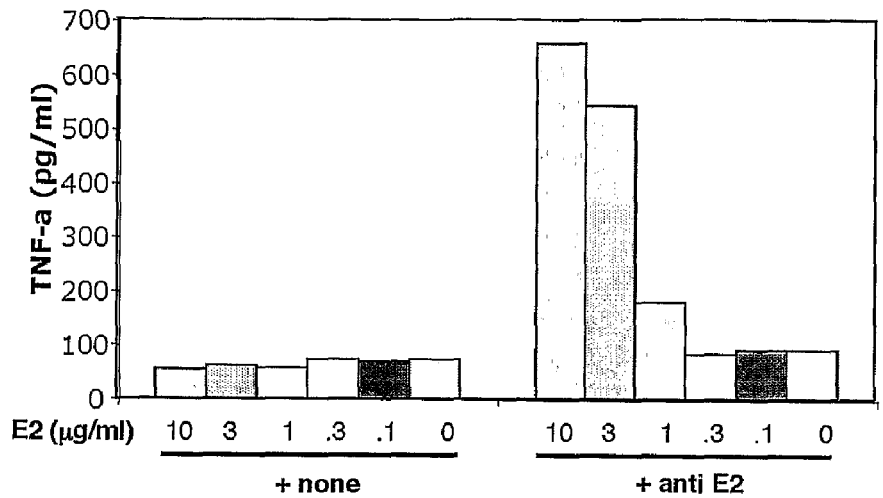
FIG. 10 shows cytokine production by T cells. PBMCs (FIGS. 10a) and c), or MACS- (magnetic activated cell sorting) purified T cells (FIG. 10b) were stimulated with combinations of mAbs or HCV E2 for 48 hours or as indicated. Cytokine secretion was assessed by ELISA.
Figure 10B:
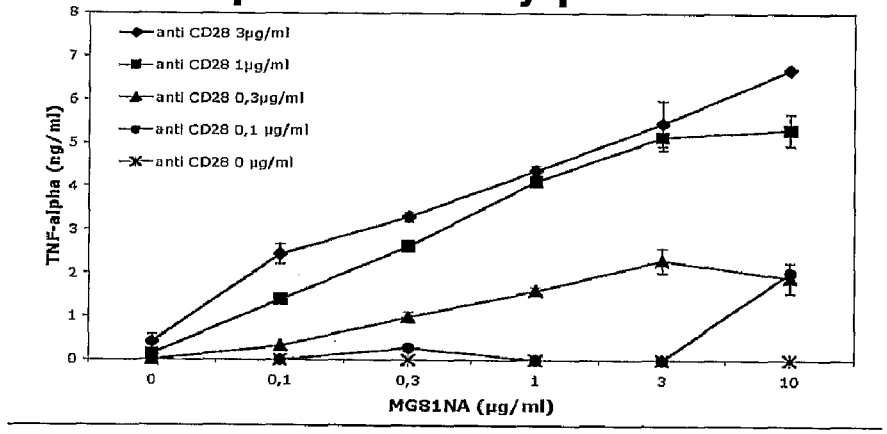
Figure 10C:
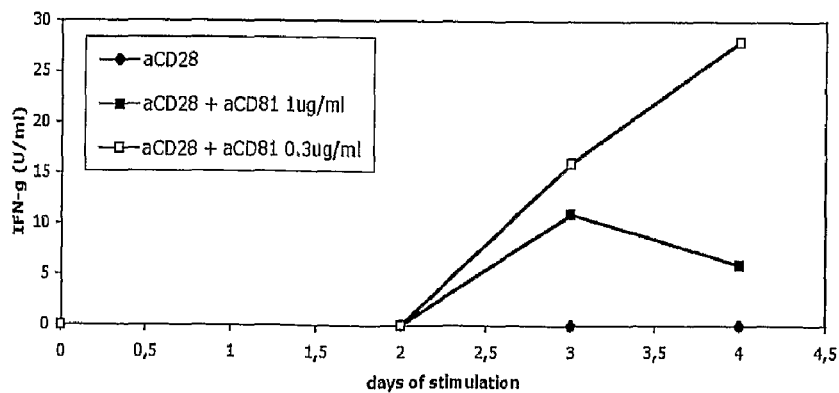

Cytokine production by T cells: PBMCs (FIG. 10a, c), or MACS-purified T cells (FIG. 10b), were stimulated with combinations of mAbs or HCV E2 for 48 hours or as indicated in FIG. 10. Cytokine secretion was measured by ELISA.

Figure 9C:
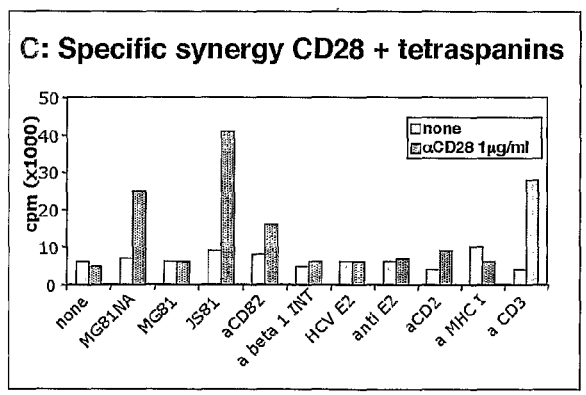
Figure 9D:
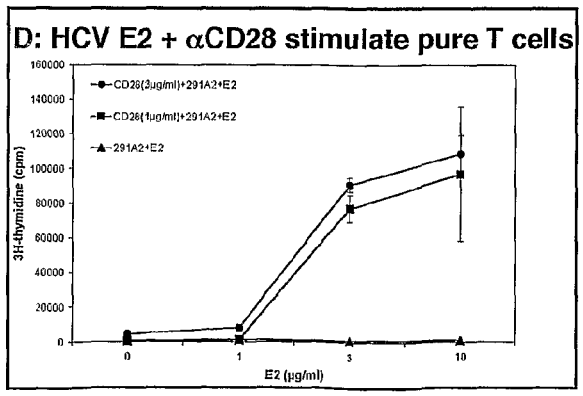

Results: Incubation of PBMCs with anti-CD28 and anti-CD81 mAbs in solution led to strong T cell proliferation, comparable to that induced by anti-CD3 mAbs (FIG. 9a, b). Ligation of the single molecules is not sufficient to induce proliferation, and a vast array of other accessory molecules such as CD2, CD5 and a number of integrins do not synergize with either CD28 or CD81 in T cell activation. In contrast, other tetraspanins, such as CD82, synergize with CD28 in T cell activation (FIG. 9c). The combined ligation of CD81 by HCV E2 together with CD28 binding also leads to T cell activation (FIG. 9D). Similarly, co-ligation of CD28 and CD81 by either HCV E2 (FIG. 10a), or by mAbs (FIG. 10b, c) stimulates production of TNF-α, IFN-γ (FIG. 10c) and other cytokines as assessed by ELISA and intracellular cytokine staining (not shown). The activation markers CD69, CD25 and CD38 were found to be up-regulated on T cells (not shown).

Figure 11A:
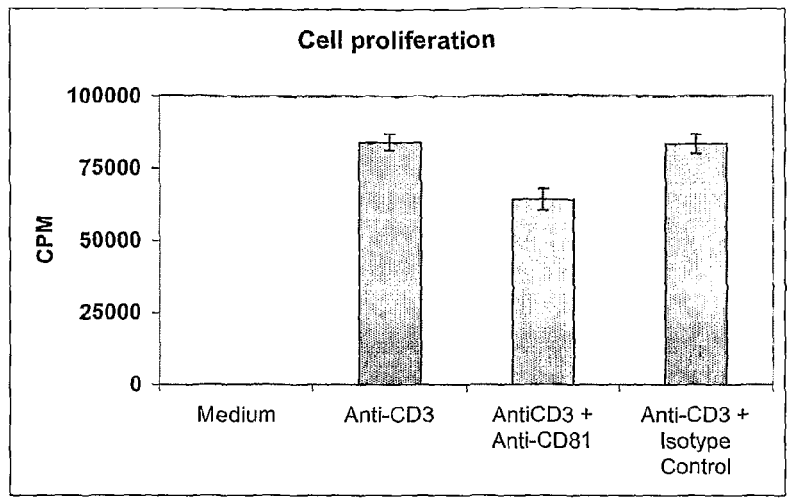
FIG. 11a shows a proliferation assay.
Figure 11B:
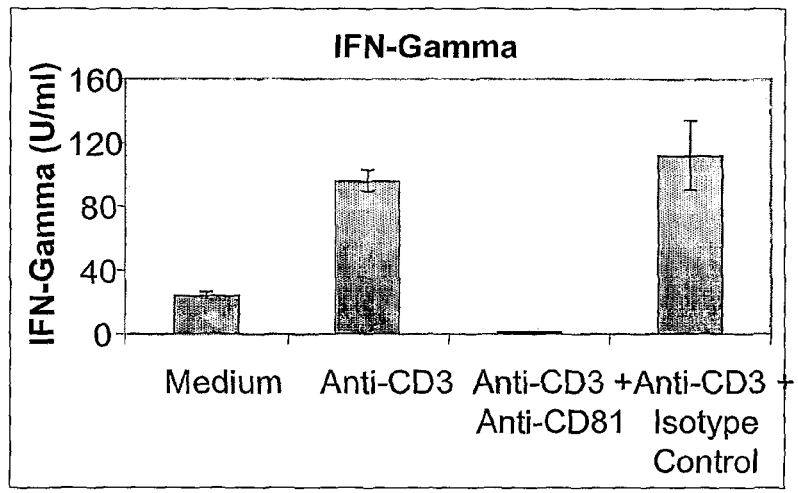
FIG. 11b shows the levels of IFNγ production.
Figure 11C:
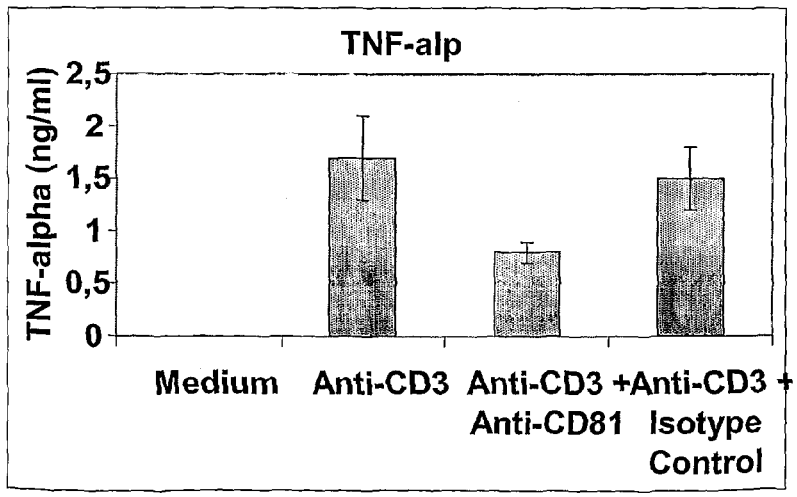
FIG. 11c shows the levels of TNFα production.

Inhibition of Cytokine Production $2 \times 10^5$ human PBMCs/well were cultured under the indicated stimuli (see FIG. 11). After 48 hrs of culture, cells were pulsed with 1 mCi/well of $^3$H-thymidine, incubated overnight and then harvested. ELISAs were performed on supernatants taken after 48 hrs of culture. The anti-CD3 mAb was present at 300 ng/ml and the anti-CD81/Isotype control was present at 1 μg/ml.

The results in FIGS. 11a), b) and c) show that ligation of CD81 with soluble mAbs inhibits CD3-dependent production of IFN-γ and TNF-α by human PBMCs.

Soluble Anti-CD81 Monoclonals Act Directly on T Cells

Human monocytes and T cells were purified by immunomagnetic cell sorting. Either type of cells were preincubated with MG81NA (an anti-CD81 mAb) (0.1 mg/ml) for 30 mins at 37° C., washed twice and then cultured either alone or in combination with the indicated cell type under different stimuli (see FIG. 12). In addition, monocytes were irradiated prior to preincubating. After 48 hrs of culture, supernatant were taken and assayed for the presence of IFN-γ.

Figure 12A:
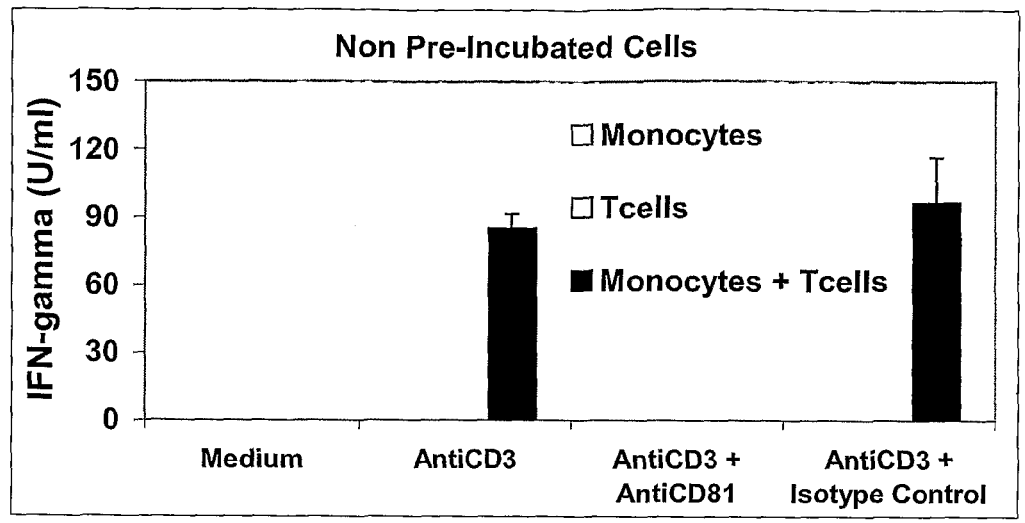
FIG. 12 shows the results of the effect of soluble anti-CD81 mAb on T cells and monocytes as a function of IFNγ production.
Figure 12B:
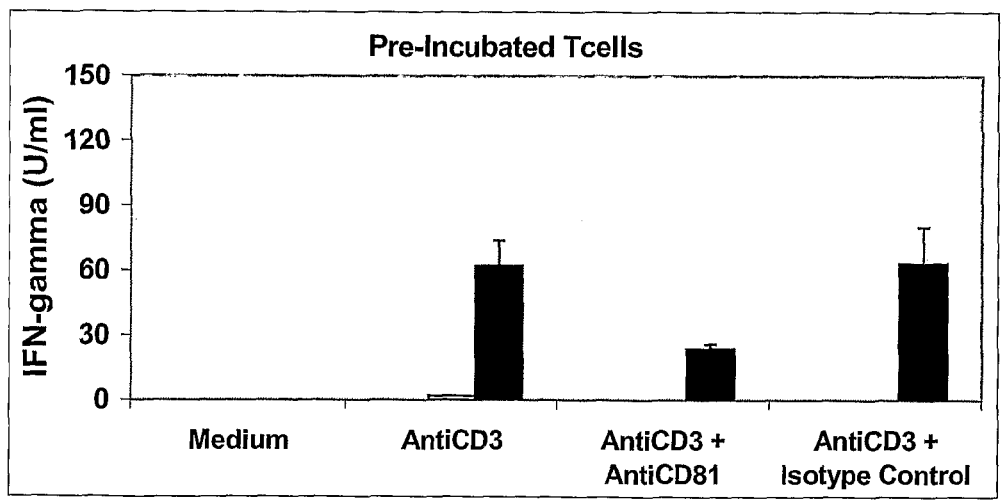
Figure 12C:
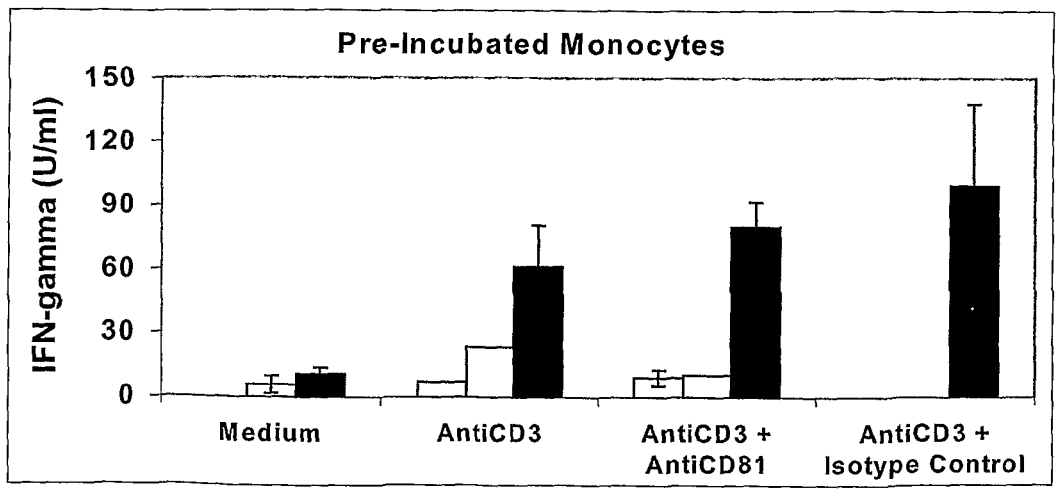

The results in FIGS. 12a), b) and c) show that the activity of soluble anti-CD81 mAbs is exerted specifically and directly on T cells.

Figure 13A:
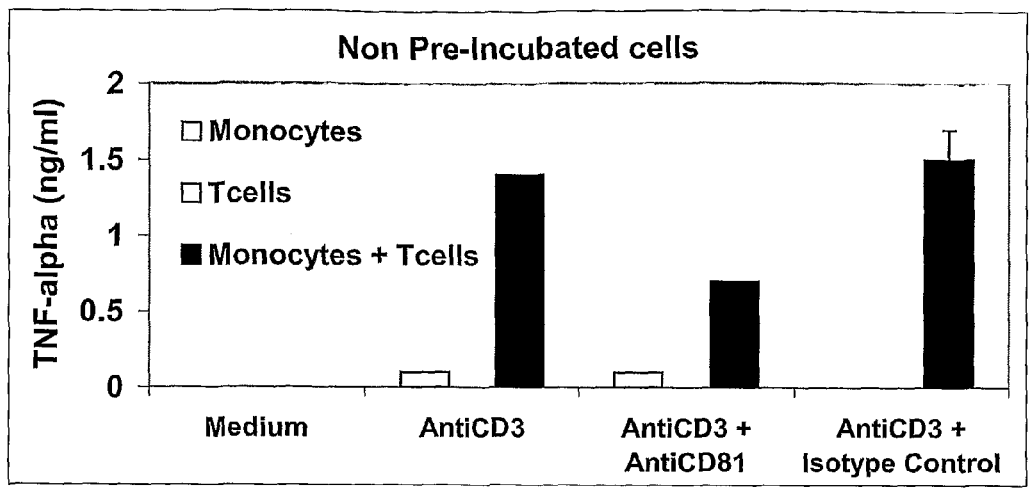
FIG. 13 shows the results of the effect of soluble anti-CD81 mAb on T cells and monocytes as a function of TNFα production.
Figure 13B:
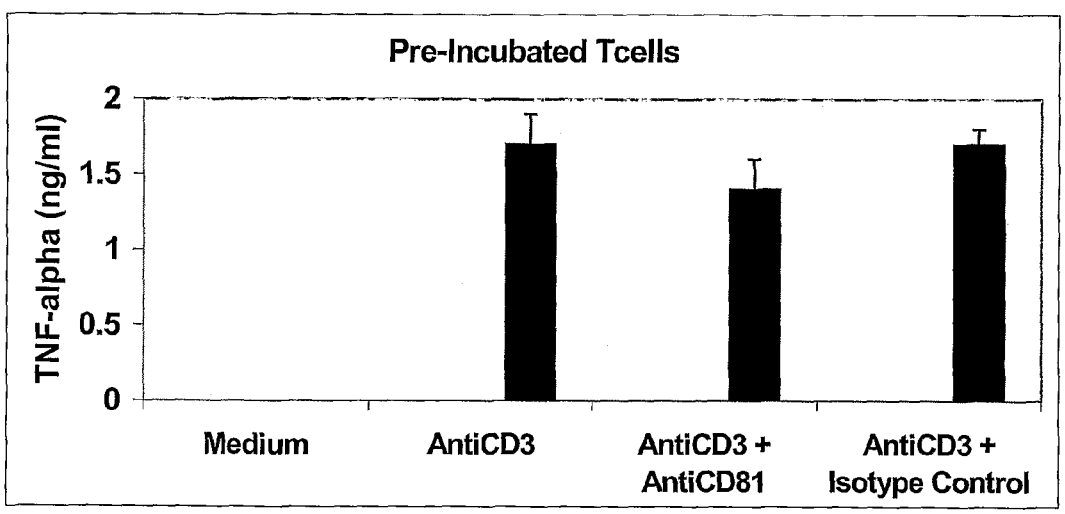
Figure 13C:
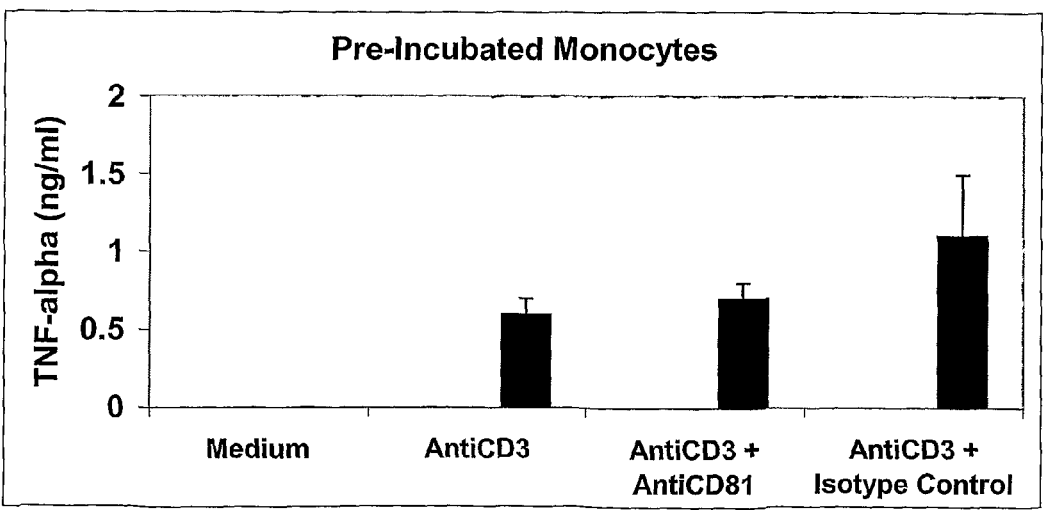

In further experiments, cells were purified and cultured as described above. After 48 hrs of culture, supernatant were taken and assayed for the presence of TNF-α. The results in FIGS. 13a), b) and c) show that the activity of soluble anti-CD81 mAbs is exerted specifically and directly on T cells.

Figure 14A:
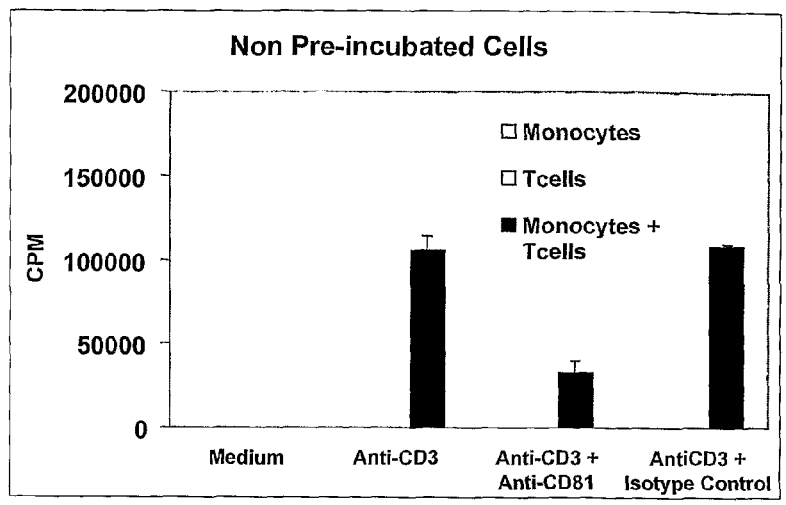
FIG. 14 shows the results of the effect of soluble anti-CD81 mAb on T cells and monocytes as a function of cell proliferation.
Figure 14B:
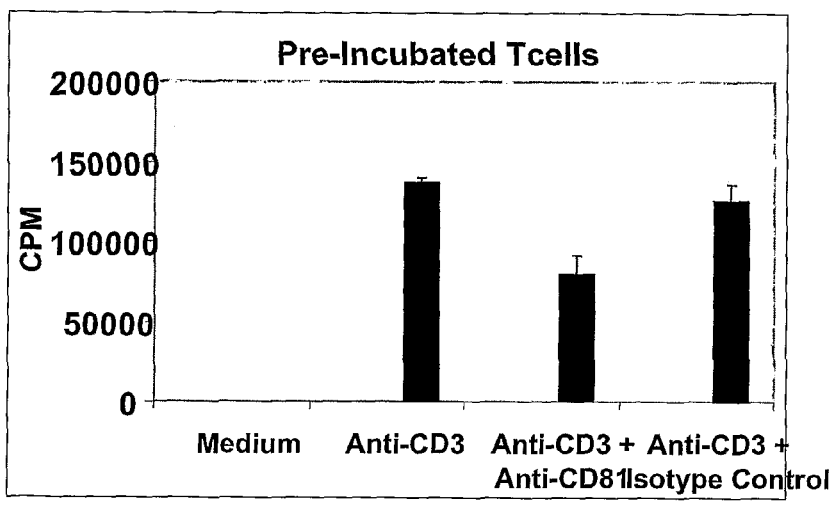
Figure 14C:
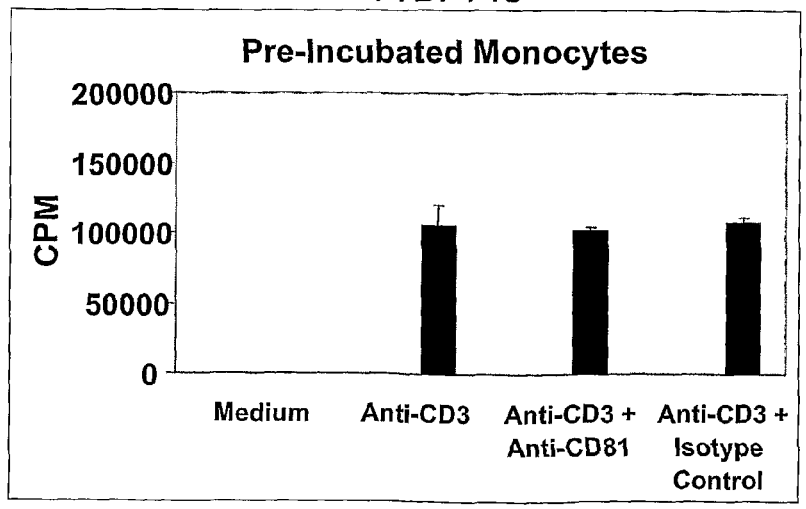

In further experiments, cells were pulsed with 1 μCi/well of ³H-thymidine after the 48 hour culture. The cells were then incubated overnight, and harvested. The level of proliferation was determined by measuring the counts per minute (CPM). The results in FIGS. 14a), b) and c) show that the activity of soluble anti-CD81 mAbs is exerted specifically and directly on T cells.

Figure 15:
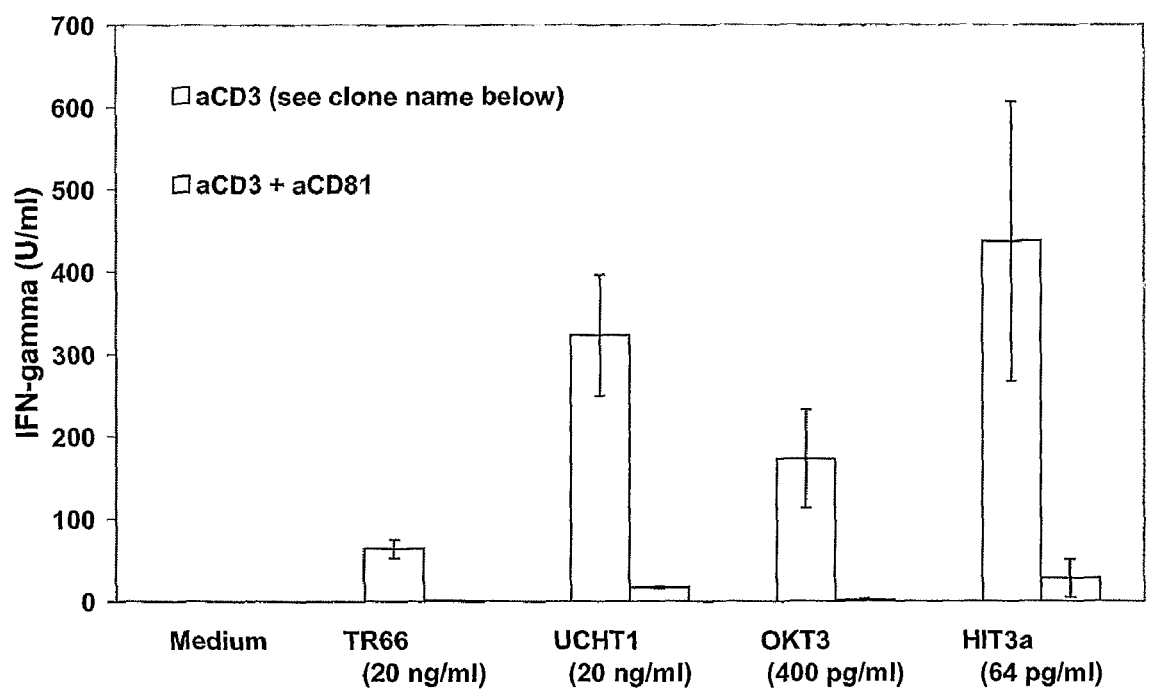
FIG. 15 shows the results of ligation of CD81 with anti-CD81 mAb and various different anti-CD3 mAbs as a function of IFNγ production.

Anti-CD81 Blocks IFNγ Secretion $2 \times 10^5$ human PBMCs/well were cultured under the indicated stimuli (see FIG. 15). Culture supernatants were taken after 48 hrs and ELISAs were performed. The anti-CD81 mAB was present at 0.1 μg/ml. OKT3 (anti-CD3) was obtained from ATCC, Rockville, Md., USA.

The results shown in FIG. 15 indicate that anti-CD81 mAbs block the induction of IFN-γ secretion by T-cells stimulated with different anti-CD3 mAbs.

Priming of Human Naïve T Cells $2 \times 10^5$ purified human CD45RO⁻ T cells from healthy adult donors were loaded with CFSE and cultured for 5 days with various combinations of anti-CD28, anti-CD81, anti-CD3 and IgG1 antibodies. At day 5, CD4⁺ (bottom row) and CD8⁺ (top row) cells were analyzed with a flow cytometer to measure their proliferation.

Figure 16:
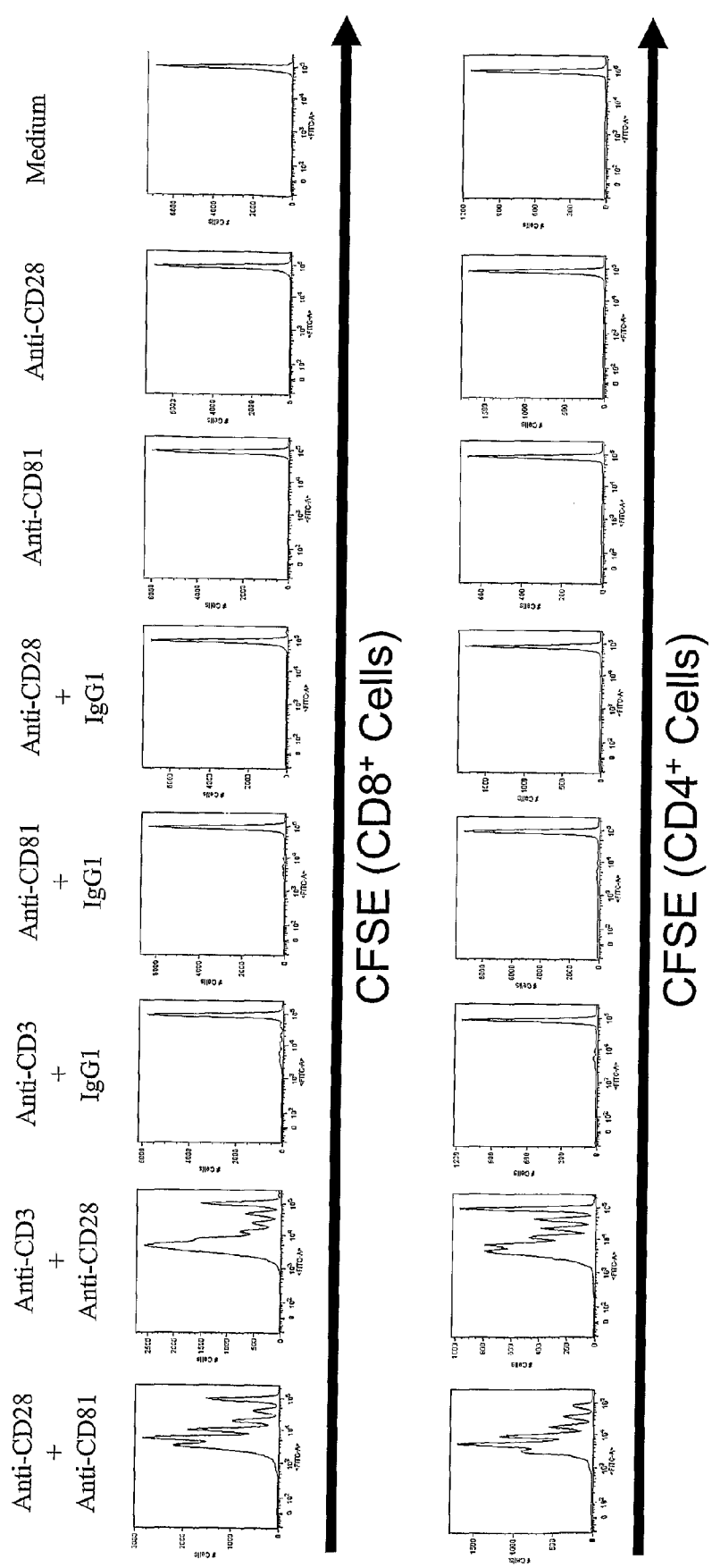
FIG. 16 shows the results of priming human naïve T cells by simultaneous binding of CD28 and CD81.

The results shown in FIG. 16 indicate that human naïve T cells can be primed by simultaneous binding of the two co-stimulatory molecules CD28 and CD81. The results show that the naïve T cells are not primed by the use of anti-CD28 or anti-CD81 alone.

Up-Regulation of Early-Intermediate Activation Markers

CD4⁺ T cells (comprising naïve and effector T cells) were purified from the blood of healthy adult donors and cultured with either a) medium, b) anti-CD28 +isotype control, c) anti-CD28 +anti-CD81 or d) anti-CD3. Cells were taken at 24 hours, 48 hours and 72 hours and stained for the surface-expression of activation markers CD25 and CD69 and then analyzed using a flow cytometer. Each plot represents $1 \times 10^4$ cells.

Figure 17:
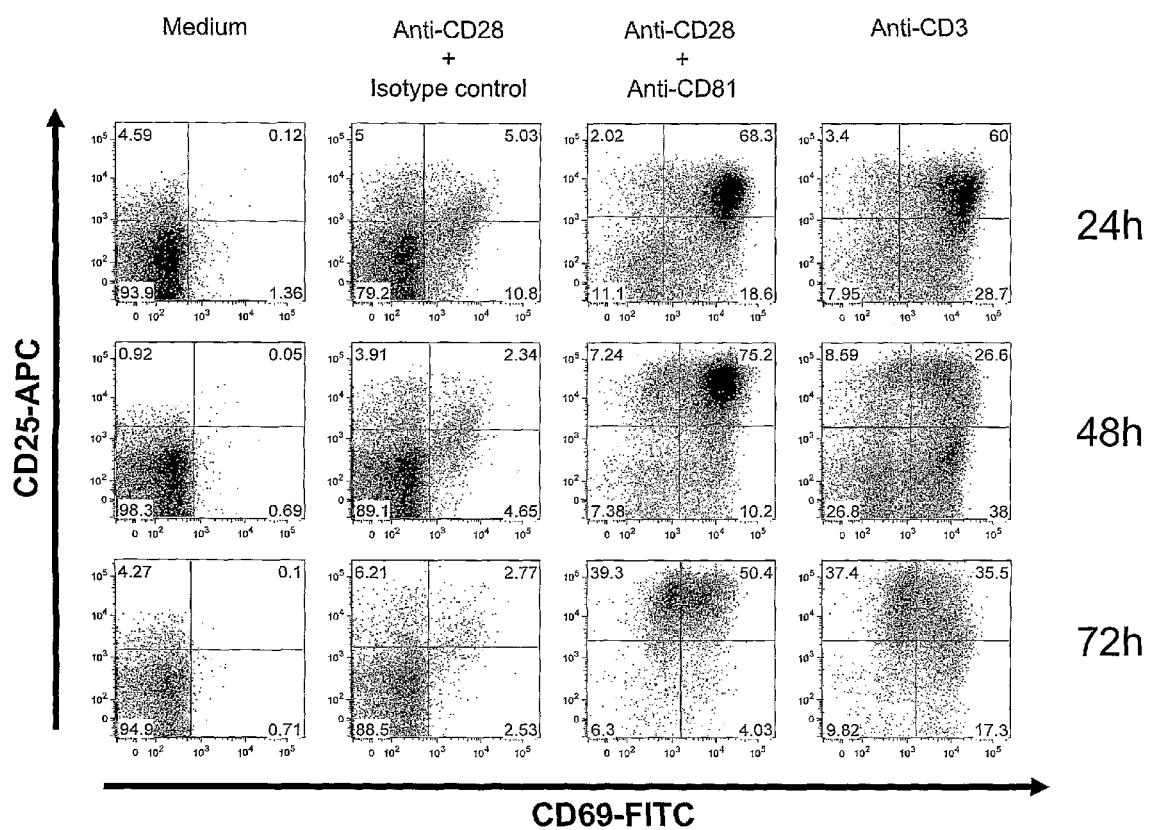
FIG. 17 shows the upregulation of early-intermediate activation markers by stimulating human CD4+ T cells with a pair of antibodies against CD28 and CD81.

The results shown in FIG. 17 indicate that stimulation of human CD4+ T cells with a pair of antibodies against CD28 and CD81 induces upregulation of early-intermediate activation markers. CD69 is an early activation marker whereas CD25 is a later activation marker. The kinetics of expression of CD69 and CD25 are consistent with what would be expected for T cell activation using TCR-dependent methods.

Expression of Effector Molecule CD40-Ligand

CD4⁺ T cells (comprising naïve and effector T cells) were purified from the blood of healthy adult donors and cultured with either a) medium, b) anti-CD28 +isotype control, c) anti-CD28 +anti-CD81 or d) anti-CD3. Cells were taken at 24 hours, 48 hours, 72 hours and 96 hours and stained for the expression of CD40-Ligand and then analyzed using a flow cytometer. Each histogram represents $1 \times 10^4$ cells.

Figure 18:
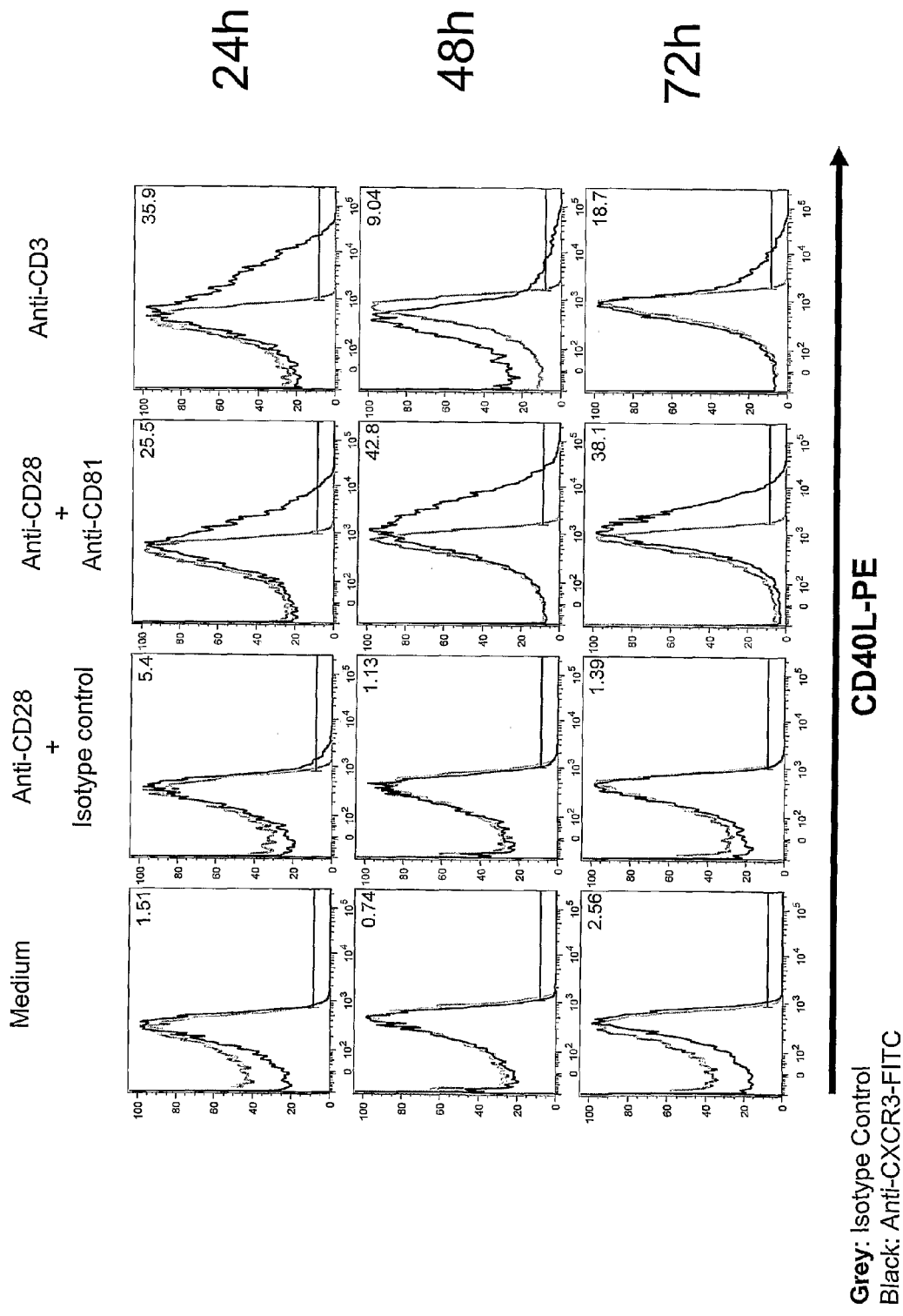
FIG. 18 shows the expression of the effector molecule CD40-ligand by stimulating human CD4+ T cells with a pair of antibodies against CD28 and CD81.

The results shown in FIG. 18 indicate that stimulation of human CD4+ T cells with a pair of antibodies against CD28 and CD81 induces expression of the effector molecule CD40-Ligand. In particular, co-ligation of CD28 and CD81 is shown to increase the expression of CD40-Ligand for a longer period of time than stimulation with anti-CD3. The expression of CD40-Ligand indicates that the T cells are able to give help to B cells.

Production of Th2-Type Cytokines

Purified human T cells were stimulated either with anti-CD3 or with anti-CD28 plus anti-CD81 for up to 72 hrs. Supernatants were taken from the cultures and assayed for the presence of Th1 or Th2 cytokines with the mesoscale system, which allows simultaneous detection of multiple cytokines from the same sample [69,70]. The amount of cytokine produced by cells stimulated with anti-CD3 (minus the background measured for unstimulated cells) was considered as 100%. The numbers on top of each grey column indicate the concentration per cytokine measured in pg/ml produced by cells stimulated with anti-CD3 and are repeated in table 1 below:

TABLE 1

| Th1 cytokine | Th2 cytokine | Concentration of cytokine |
|---|---|---|
| IFN-γ | | 50000 pg/ml |
| IL-1β | | 2.4 pg/ml |
| IL-2 | | 2000 pg/ml |
| TNFα | | 2300 pg/ml |
| | IL-4 | 33 pg/ml |
| | IL-5 | 162 pg/ml |
| | IL-8 | 228 pg/ml |
| | IL-10 | 7700 pg/ml |
| | IL-13 | 1700 pg/ml |

Figure 19:
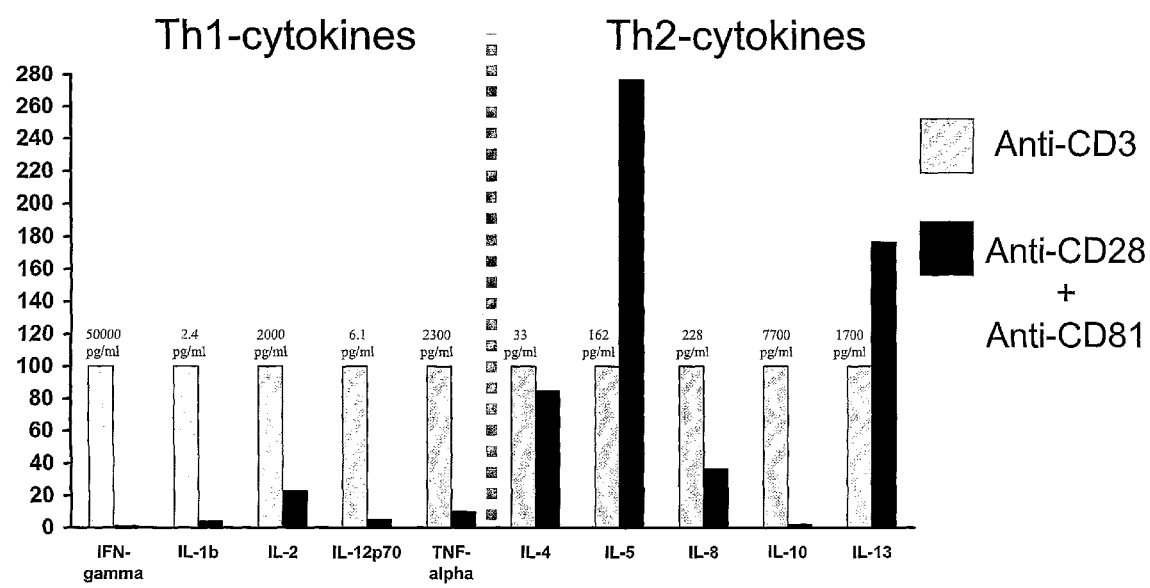
FIG. 19 shows the preferential production of Th2-type cytokines by stimulating human T cells by simultaneous engagement of CD28 and CD81.

The results in FIG. 19 show that stimulation of human T cells by simultaneous engagement of CD28 and CD81 induces preferential production of Th2-type cytokines as compared to Th1 cytokines. This indicates that simultaneous engagement of CD28 and CD81 induces a Th2 profile rather than a Th1 profile. The Th2 profile here includes secretion of IL-4, IL-5, IL-8 and IL-13. These results show a particularly high expression of IL-5 and IL-13 resulting from co-stimulation with anti-CD28 and anti-CD81 as compared to stimulation with anti-CD3. This suggests that the TCR-independent stimulation of the present invention is particularly useful where high levels of IL-5 and/or IL-13 are required.

The experiments for which the results are shown in FIG. 19 were carried out on total T cell populations from healthy individuals. Anti-CD28 was given at a submitogenic dose and so all of the effects observed are due to the synergy between CD28 and CD81 only. The results in FIG. 19 clearly show that the cells are producing type 2 cytokines in a predominant manner. The data presented in FIG. 19 suggest that co-ligation of CD28 and CD81 may induce type 1 cells to switch to type 2 cells.

Upregulation of Chemokine Receptors Characteristic of a Th2 Profile

CD4⁺ T cells were purified from the blood of healthy adult donors and cultured with different stimuli (a: medium; b: anti-CD28 +isotype control; c: anti-CD28 +anti-CD81; and d) anti-CD3). Cells were taken at 24 hours, 48 hours and 72 hours and stained for the expression of CCR4 (a type 2 marker) and then analyzed using a flow cytometer. Each histogram represents $1 \times 10^4$ cells.

Figure 20:
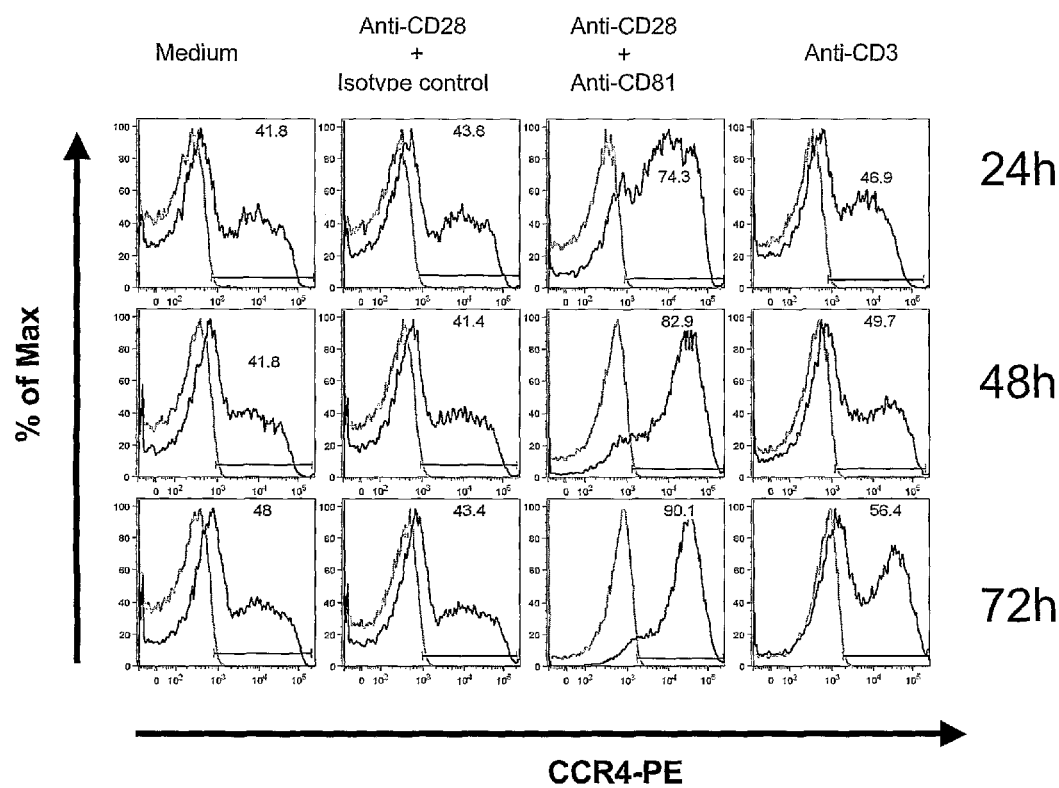
FIG. 20 shows the upregulation of chemokine receptors characteristic of a Th2 profile by stimulating human CD4+ T cells with a pair of antibodies against CD28 and CD81.

The results shown in FIG. 20 indicate that simulation of human CD4+ T cells with a pair of antibodies against CD28 and CD81 induces upregulation of chemokine receptors characteristic of a Th2 profile.

The experiments for which the results are shown in FIG. 20 were carried out on total T cell populations from healthy individuals. Anti-CD28 was given at a submitogenic dose and so all of the effects observed are due to the synergy between CD28 and CD81 only. The flow cytometry data in FIG. 20 indicate that almost all (about 90%) of the cells present in the culture that were stimulated with anti-CD28 and anti-CD81 express CCR4 at high levels. CCR4 is a chemokine receptor strongly associated with Th2 memory cells [24, 71].

Expression of Chemokine Receptors on Naïve T Cells

Human CD45RO negative CD8 T cells (top row of FIG. 21) and human CD45RO negative CD4 T cells (bottom row of FIG. 21) were cultured with anti-CD3 +anti-CD28 or with anti-CD28 +anti-CD81. The expression of CCR4 (a chemokine receptor which is a type 2 marker) and CXCR3 (a chemokine receptor which is a type 1 marker), were measured at day 0 and again on day 4.

Figure 21:
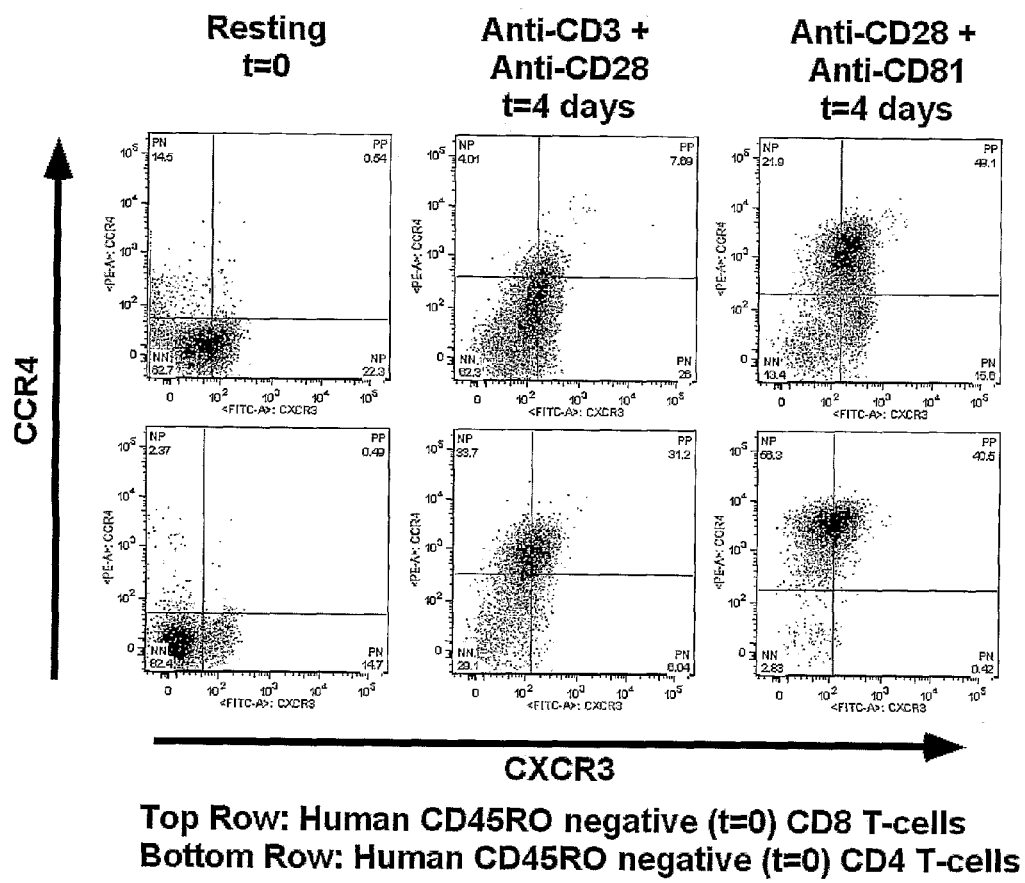
FIG. 21 shows the expression of chemokine receptors on naïve T cells primed by engagement of CD28 and CD81.

The results shown in FIG. 21 indicate that engagement of CD28 and CD81 only marginally increased the expression of the type 1 marker (CXCR3), but significantly increased the expression of the type 2 marker (CCR4). Further, the expression of both the type 2 marker and the type 1 marker was increased by a greater extent by co-ligation of CD28 and CD81 than with co-ligation of CD3 and CD28, suggesting that the co-ligation of CD81 and CD28 is a more effective method of activating T cells than through TCR-dependent activation. In particular, induction of a type 2 profile (Th2 or Tc2) was increased to a greater extent with co-ligation of CD81 and CD28 than with co-ligation of CD3 and CD28.

Expression of Activation Markers on Naïve T Cells

Human CD45RO negative CD8 T cells (top row of FIG. 22) and human CD45RO negative CD4 T cells (bottom row of FIG. 22) were cultured with anti-CD3 +anti-CD28 or with anti-CD28 +anti-CD81. The expression of the activation marker CD25 was measured at day 0 and again on day 4.

Figure 22:
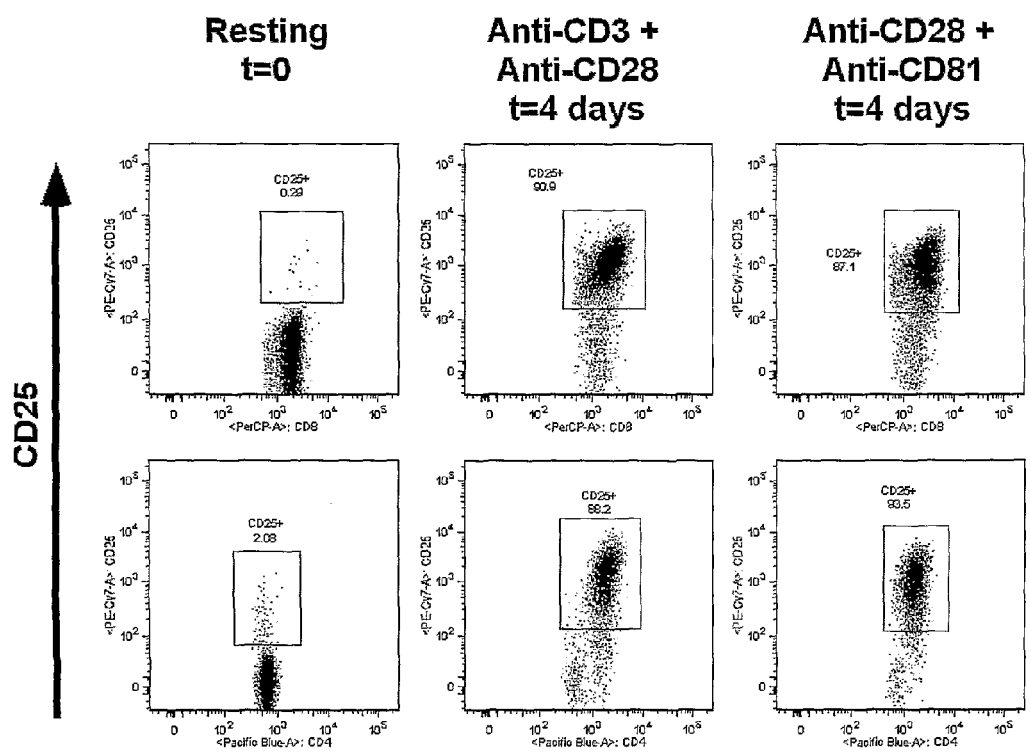
FIG. 22 shows the expression of activation markers on naïve T cells primed by engagement of CD28 and CD81.

The results shown in FIG. 22 indicate that co-engagement of CD28 and CD81 induces the expression of activation markers on naïve T cells to a similar extent as co-engagement of CD3 and CD28. The results in FIG. 22 act as a control for the results in FIG. 21 as they show that the results in FIG. 21 are not dependent on the level of activation of the cells.

Upregulation of Chemokine Receptors $CD4^+$ T cells (comprising naïve and effector cells) were purified from the blood of healthy adult donors and cultured with different stimuli (a: medium; b: anti-CD28 +isotype control; c: anti-CD28+anti-CD81; d: anti-CD3). Cells were taken at 24 hours, 48 hours and 72 hours and stained for the expression of CXCR3 (a chemokine receptor) and then analyzed using a flow cytometer. Each histogram represents $1 \times 10^4$ cells.

Figure 23:
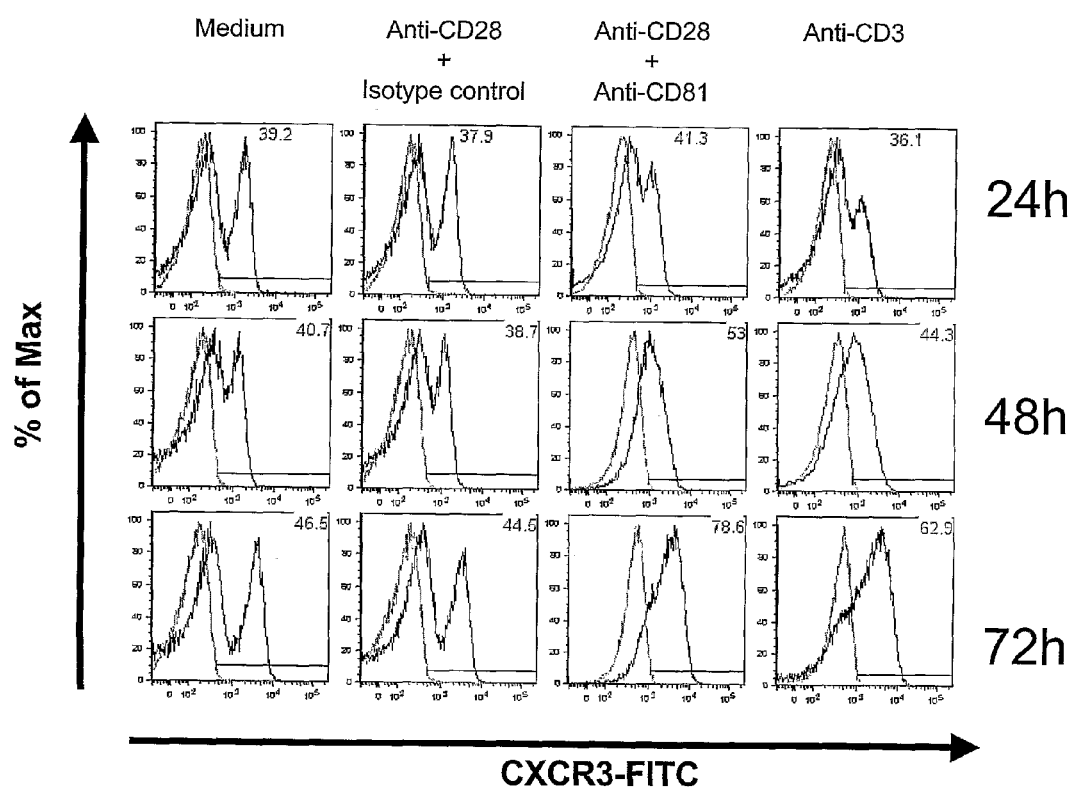
FIG. 23 shows the upregulation of chemokine receptors by stimulating human CD4+ T cells with a pair of antibodies against CD28 and CD81.

The results shown in FIG. 23 indicate that stimulation of human CD4+ T cells with a pair of antibodies against CD28 and CD81 induces upregulation of chemokine receptors.

No Internalisation of the T Cell Receptor

Human $\alpha\beta$-$TCR^+$ $\gamma\delta$-$TCR^-$ T cells were purified from the blood of healthy adult donors and cultured under different stimuli (bottom left). At the indicated time points (top), cells were taken and stained for the level of expression of CD25, CD69, the $\alpha\beta$-TCR and then analyzed using a flow cytometer. Negative controls were analyzed in the $CD25^-CD69^-$ double negative gate, whereas stimulated cells were gated on the $CD25^+CD69^+$ double positive population. Each histogram represents $1 \times 10^4$ gated cells.

Figure 24:
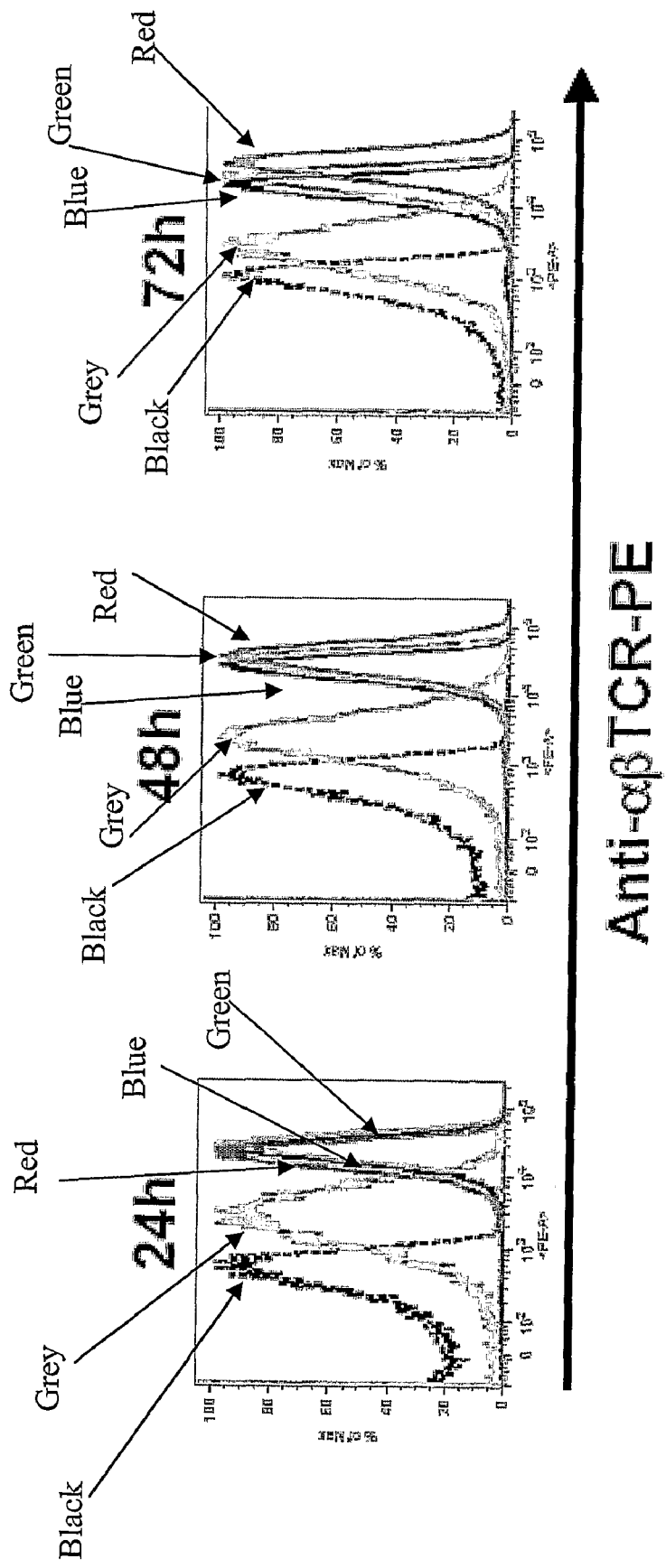
FIG. 24 shows that activation of human αβ-T cells by simultaneous engagement of CD28 and CD81 does not cause internalization of the T cell receptor.

The results shown in FIG. 24 indicate that activation of human $\alpha\beta$-T cells by simultaneous engagement of CD28 and CD81 does not cause internalization of the T cell receptor, suggesting the induction of a novel signaling pathway independent from upstream events triggered by recognition of antigen.

Production of Type-2 Effector Cytokines

Naive human $CD8^+$ T cells were stimulated with a variety of stimuli (first column: plastic-bound anti-CD3 +costimulatory anti-CD28 in non-polarizing conditions; second column: Tc1 polarizing conditions; third column: Tc2 polarizing conditions; fourth column: plastic-bound anti-CD81 plus soluble superagonist anti-CD28). After 6 days, the cells were expanded in IL-2 for another 7-10 days depending on the initial conditions. Then cells were re-stimulated with PMA and Ionomycin for 6 hours. Brefeldin-A was added during the last 4 hours, followed by detection of intracellular cytokines by flow cytometry. Cells were stained with anti-human IFN-$\gamma$ versus either human IL-4+IL13 (top), IL-5 (middle) and IL-2 (bottom).

Figure 25:
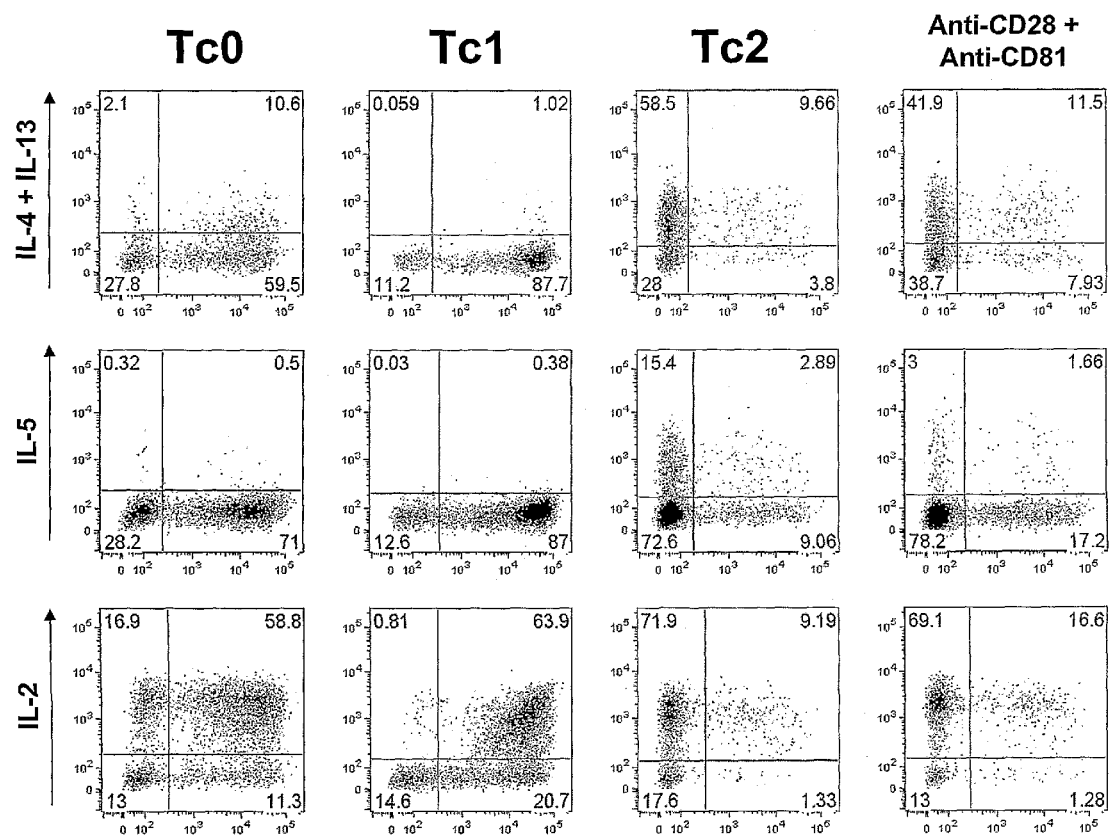
FIG. 25 shows the production of type 2 cytokines by priming CD8+ T cells by co-engagement of CD28 and CD81.

The results shown in FIG. 25 indicate that CD8+ T cells primed by co-engagement of CD28 and CD81 produce type 2 (Tc2) effector cytokines. Although CD8+ T cells primed by co-engagement of CD28 and CD81 produced IFN-$\gamma$ (a type 1 marker), it was produced in low amounts. In contrast, type 2 cytokines, such as IL-4, IL-5, IL-8 and IL-13, were predominant.

A further experiment was conducted in which naive human $CD4^+$ T cells were stimulated either with plastic-bound anti-CD81 plus soluble superagonist anti-CD28 (4th column of FIG. 26) or with a) plastic-bound anti-CD3+costimulatory anti-CD28 in non-polarizing conditions (first column), b) Th1 polarizing conditions (second column), or c) Th2 polarizing conditions (third column). After 6 days, cells were expanded in IL-2 for another 7-10 days, depending on the initial conditions. Then cells were re-stimulated with PMA and Ionomycin for 6 hours. Brefeldin-A was added during the last 4 hours, followed by detection of intracellular cytokines by flow cytometry. Cells were stained with anti-human IFN-$\gamma$ versus either human IL-4 (top) and IL13 (middle), or TNF-$\gamma$ versus IL-2 (bottom). The results of this further experiment are shown in FIG. 26.

Figure 26:
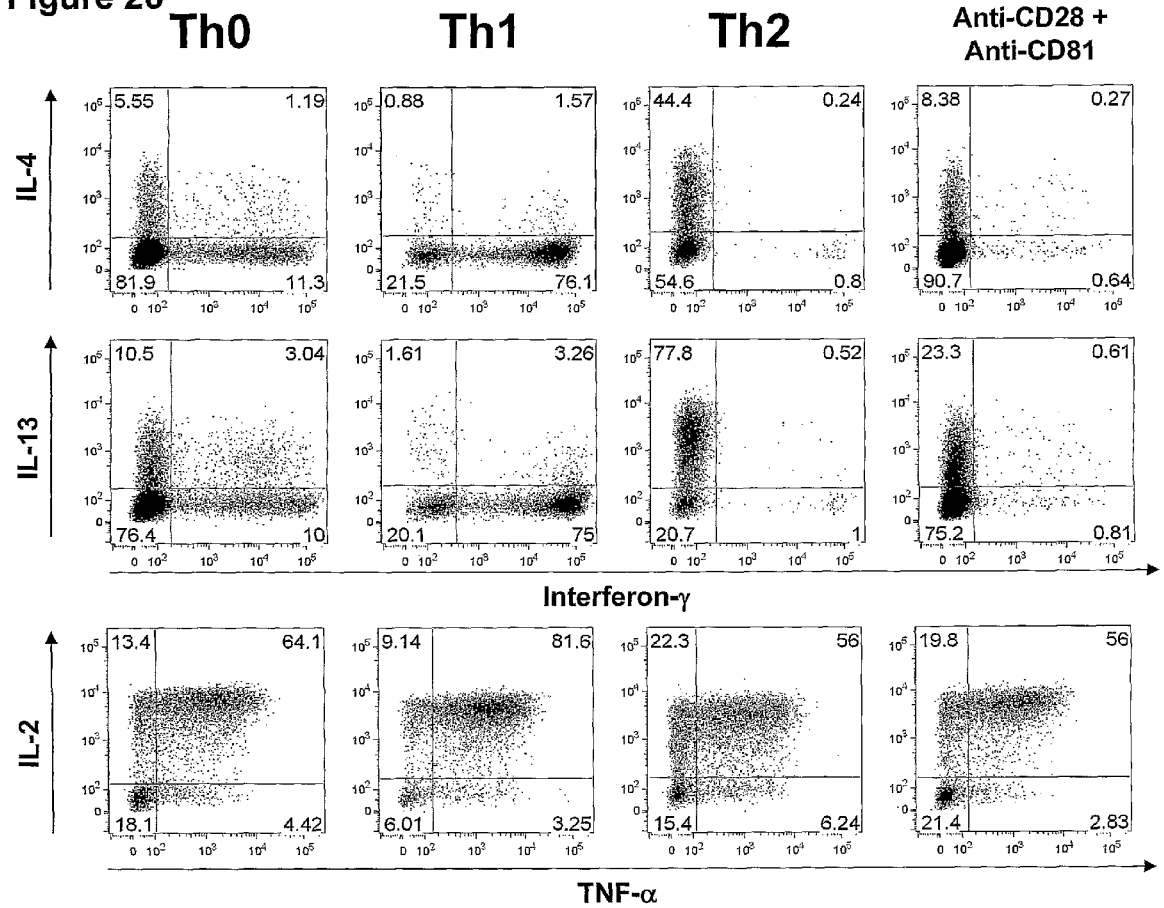
FIG. 26 shows the production of type 2 cytokines by priming CD4+ T cells by co-engagement of CD28 and CD81.

The results shown in FIG. 26 indicate that naive human CD4+ T cells become polarized when they are primed by co-engagement of CD28 and CD81. The data show that the naive human CD4+ T cells polarize toward the Th2 effector type.

Summary

In summary, the production of cytokines by co-ligation of CD28 and CD81 was compared with the production of cytokines by ligation of CD3. Ligation of CD3 is involved in TCR-dependent T cell activation. The data suggest that stimulation of T cells by co-ligation of CD28 and CD81 results in differentiation into T cells having a Th2 profile (for CD4+ T cells) or Tc2 cells (for CD8+ T cells). Differentiation into these Th2 or Tc2 profiles was not found when naïve T cells were stimulated with CD28 or CD81 alone.

It will be understood that the invention has been described by way of example only and modifications may be made whilst remaining within the scope and spirit of the invention.

REFERENCES (THE CONTENTS OF WHICH ARE HEREBY INCORPORATED IN FULL)

[1] Marinari, B. et al., PNAS USA, 101(16): 6098-6103, 2004.
[2] Skapenko et al., (J. Immunol., 166(7): 4283-4292, 2001)
[3] Wack, A. et al., Eur. J. Immunol., 2001, 31(1), 166-175
[4] Tseng, C. T. et al., Cell Immunol., 2001, 207(1), 19-27.
[5] Tsitsikov, E. N. et al., PNAS USA, 1997, 94(20): 10844-10849
[6] Maecker, H. T. and Levy, S., J. Exp. Med., 1997, 185(8), 1505-1510
[7] Miyazaki, T. et al., EMBO J., 1997, 16(14): 4217-4225
[8] Tardiff and Tremblay (J. Virol. 79(9): 4316-4328, 2005)
[9] Deng, J. et al., Int. Immunol. 2002, 14(5): 513-523.
[10] Maecker, H. T., et al., PNAS USA, 1998, 95(5), 2458-2462
[11] Deng J. et al., J. Immunol., 2000, 165(9): 5054-5061
[12] Pileri et al. Science. Oct. 30, 1998; 282(5390):938-41.
[13] Witherden et al. (2000) The Journal of Immunology, 2000, 165: 1902-1909.
[14] Laskowski et al. J Am Soc Nephrol 13:519-527, 2002
[15] Bonyhadi J Immunol Feb. 15, 2005; 174(4):2366-75

[16] Luhder, F. et al., (J. Exp. Med., 2003, 197(8): 955-966.
[17] Davis et al. *Acta Crystallogr D Biol Crystallogr.* April 2001; 57(Pt 4):605-8
[18] Todo et al. Cancer Res. Jan. 1, 2001; 61(1):153-61
[19] Gerstmayer et al. FEBS Lett. Apr. 21, 1997; 407(1):63-8
[20] Hock et al.—Leukemia. May 2002; 16(5):865-73
[21] Flo et al. Cell Immunol. May 1, 2001; 209(2):120-31
[22] Jeannin et al. Immunity. September 2000; 13(3):303-12
[23] Liew F Y, Nat Rev Immunol. January 2002; 2(1):55-60
[24] O'Garra et al., Curr. Biol. Sep. 10, 1998; 8(18):R646-9
[25] Grogan J L et al., Immunity. March 2001; 14(3):205-15
[26] Whary, M T et al., Curr. Top. Med. Chem. 2004;4(5): 531-8, review
[27] Singh, V K et al., Immunol. Res. 1999, 20(2): 147-171, review
[28] O'Garra, A et al., Curr. Opin. Immunol. 1997, 9(6):872-883, review
[29] Nicholson, L B et al. Curr. Opin. Immunol., 1996, 8(6): 837-842, review
[30] Charlton, B. et al. Curr. Opin. Immunol. 1995, 7)6): 793-798, review
[31] Druet, P. et al. Clin. Exp. Immunol. 1995, 101, Suppl. 1:9-12
[32] Gennaro (2000) *Remington: The Science and Practice of Pharmacy,* 20th edition, ISBN: 0683306472.
[33] Kabat et al., 1987, in Sequences of Proteins of Immunological Interest, US Department of Health and Human Services, NIH, USA
[34] Breedveld (2000) *Lancet* 355(9205):735-740.
[35] Gorman & Clark (1990) *Semin. Immunol.* 2:457-466
[36] Jones et al. *Nature* 321:522-525 (1986)
[37] Morrison et al., *Proc. Natl. Acad. Sci, US.A.,* 81:6851-6855 (1984)
[38] Morrison & Oi, *Adv. Immunol.,* 44:65-92 (1988)
[39] Verhoeyer et al., *Science* 239:1534-1536 (1988)
[40] Padlan, *Molec. Immun.* 28:489-498 (1991)
[41] Padlan, *Molec. Immunol.* 31(3):169-217 (1994).
[42] Kettleborough et al., *Protein Eng.* 4(7):773-83 (1991).
[43] WO 98/24893
[44] WO 91/10741
[45] WO 96/30498
[46] WO 94/02602
[47] U.S. Pat. No. 5,939,598.
[48] Conrath et al. (2003) *Dev Comp Immunol* 27:87-103.
[49] Muyldermans (2001) *J Biotechnol* 74:277-302.
[50] Huston et al. (1988) *Proc. Nat. Acad. Sci. USA* 85:5879-5883.
[51] U.S. Pat. No. 5,091,513
[52] U.S. Pat. No. 5,132,405
[53] U.S. Pat. No. 4,946,778
[54] Pack et al., (1992) *Biochem* 31:1579-1584
[55] Cumber et al. (1992) *J. Immunology* 149B:120-126
[56] Radrizzani M et al., (1999) *Medicina (B Aires)* 59(6): 753-8.
[57] Radrizzani M et al., (2000) *Medicina (B Aires)* 60 Suppl 2:55-60.
[58] U.S. Pat. No. 4,011,308
[59] U.S. Pat. No. 4,722,890
[60] U.S. Pat. No. 4,016,043
[61] U.S. Pat. No. 3,876,504
[62] U.S. Pat. No. 3,770,380
[63] U.S. Pat. No. 4,372,745
[64] Kohler & Milstein (1975) *Nature* 256:495-497
[65] Rosa D et al. Proc Natl Acad Sci USA. Dec. 20, 2005; 102(51):18544-9
[66] Masciopinto, F. et al., Eur. J. Immuno. 2004, 34: 2834-2842;
[67] Soldaini, E. et al., Eur. J. Immuno. 2003, 33: 455-464;
[68] Bortoletto, N. et al., Eur. J. Immuno., 2002, 32(11): 3102-3107
[69] Debad, J. D. et al (2004) In Electrogenerated Chemiluminescence, ed. A.J. Bard. Marcel Dekker, New York, pp. 43-78.
[70] www.mesoscale.com/CatalogSystemWeb/WebRoot/literature/applications/pdf/ Cytokines_2005.pdf
[71] Rivino et al., J. Exp. Med. 2004, 20, 200(6):725-735

The invention claimed is:

1. A method for TCR-independent T cell activation which comprises the co-ligation of CD28 and CD81, wherein co-ligation is performed with monoclonal antibodies, wherein the monoclonal antibodies consist of a monoclonal anti-CD28 antibody and a monoclonal anti-CD81 antibody.

2. A method according to claim 1, wherein one or more of the monoclonal antibodies have a human constant region.

3. A method according to claim 1, which is carried out in vivo.

4. A method according to claim 1, which is carried out in vitro.

5. A method according to claim 3, wherein CD28 is ligated using a soluble phase anti-CD28 monoclonal antibody and CD81 is ligated using a solid-phase anti-CD81 monoclonal antibody.

6. A method according to claim 1 for the TCR-independent activation of αβ3 T cells.

7. A method according to claim 1, for the TCR-independent activation of naïve T cells.

8. A method according to claim 1, wherein the T cells are activated to switch type 1 cells to type 2 cells.

9. A method according to claim 1, where the T cells are activated to produce a Th2 or Tc2 response.

10. A method according to claim 1, wherein the T cells to be activated are CD4+ T cells.

11. A method according to claim 1, for the activation of T cells that have already differentiated into type 2 cells.

12. A method according to claim 1, for the activation of human T cells.

* * * * *